(12) United States Patent
Higashionji et al.

(10) Patent No.: US 7,982,623 B2
(45) Date of Patent: Jul. 19, 2011

(54) RADIO-TYPE TRANSMITTING DEVICE, CONTAINER, TRANSMITTING/RECEIVING SYSTEM AND TRANSMITTING/RECEIVING METHOD

(75) Inventors: Masaru Higashionji, Osaka (JP); Kenji Hasegawa, Osaka (JP); Masaru Odagiri, Hyogo (JP); Masafumi Shimotashiro, Osaka (JP); Hiroshi Seki, Nara (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/890,265

(22) Filed: Sep. 24, 2010

(65) Prior Publication Data

US 2011/0074551 A1 Mar. 31, 2011

Related U.S. Application Data

(62) Division of application No. 11/478,845, filed on Jul. 3, 2006, now Pat. No. 7,821,410.

(30) Foreign Application Priority Data

Jul. 4, 2005 (JP) ................ P2005-195122
Jun. 12, 2006 (JP) ................ P2006-162553

(51) Int. Cl.
*G08B 21/00* (2006.01)

(52) U.S. Cl. ..... 340/612; 340/618; 340/603; 340/572.1; 73/290 R

(58) Field of Classification Search ............... 340/572.1, 340/572.7, 612, 618, 603, 623, 624, 539.23, 340/572.4, 572.5, 572.8; 73/290 R, 304 C, 73/124, 662, 687, 686, 658, 657, 76.75; 200/61.45
See application file for complete search history.

(56) References Cited

U.S. PATENT DOCUMENTS

| | | | | |
|---|---|---|---|---|
| 5,640,684 A | * | 6/1997 | Konosu et al. | ............... 455/67.7 |
| 5,715,275 A | * | 2/1998 | Emi | ............... 375/134 |
| 5,799,245 A | * | 8/1998 | Ohashi | ............... 455/69 |
| 5,862,181 A | * | 1/1999 | Ishizuka | ............... 375/259 |
| 6,546,795 B1 | | 4/2003 | Dietz | |
| 7,107,836 B2 | | 9/2006 | Brookner | |
| 7,142,124 B2 | | 11/2006 | Chi et al. | |
| 2004/0004545 A1 | | 1/2004 | Early | |

FOREIGN PATENT DOCUMENTS

JP 6-325229 A 11/1994
JP 9-130999 A 5/1997

* cited by examiner

*Primary Examiner* — Anh V La
(74) *Attorney, Agent, or Firm* — McDermott Will & Emery LLP

(57) ABSTRACT

A radio-type transmitting device capable of transmitting information other than information in an internal memory is provided. A RFID tag includes a encoding circuit for digitalizing receiving sensitivity of a radio wave sent from an external transmitting/receiving apparatus and then sending the digitalized receiving sensitivity to the external transmitting/receiving apparatus. Thus, the external transmitting/receiving apparatus can obtain a distance between the external transmitting/receiving apparatus and the RFID tag based on received sensitivity information.

10 Claims, 17 Drawing Sheets

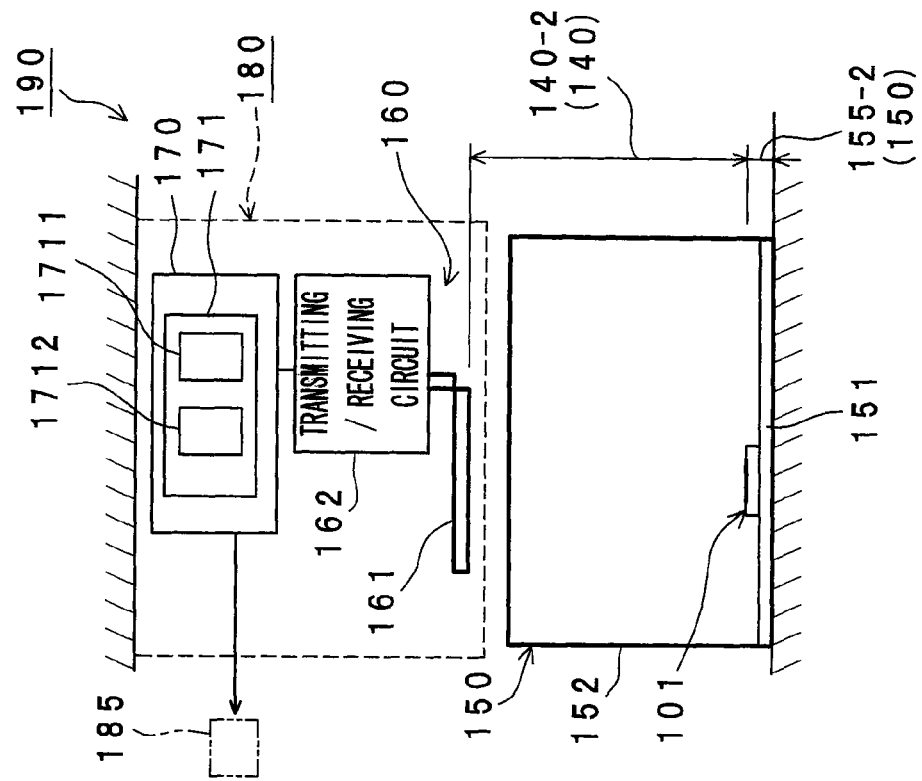
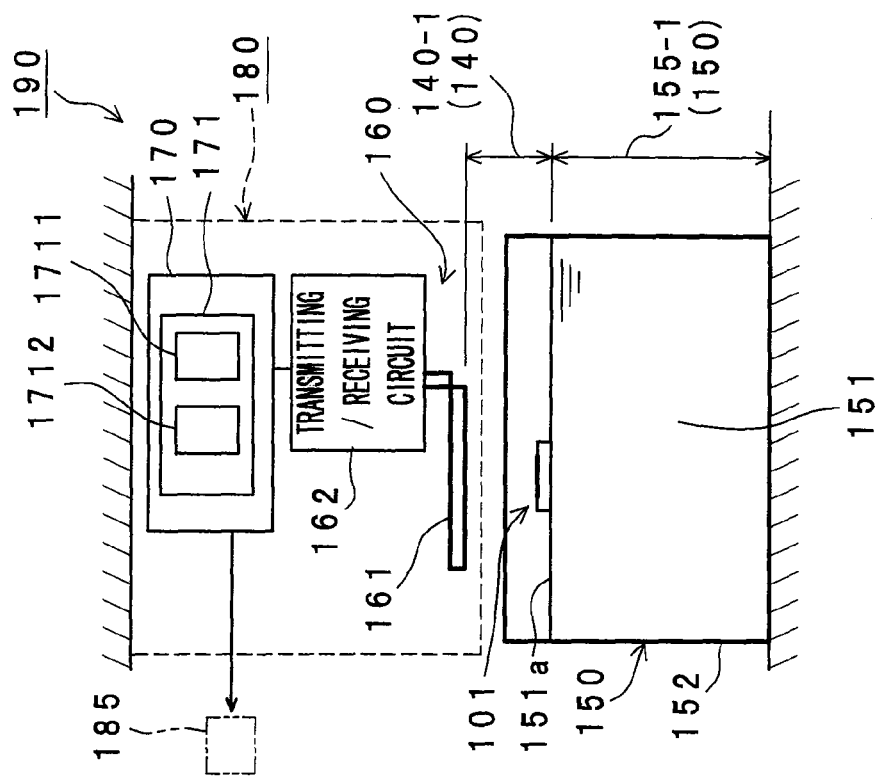

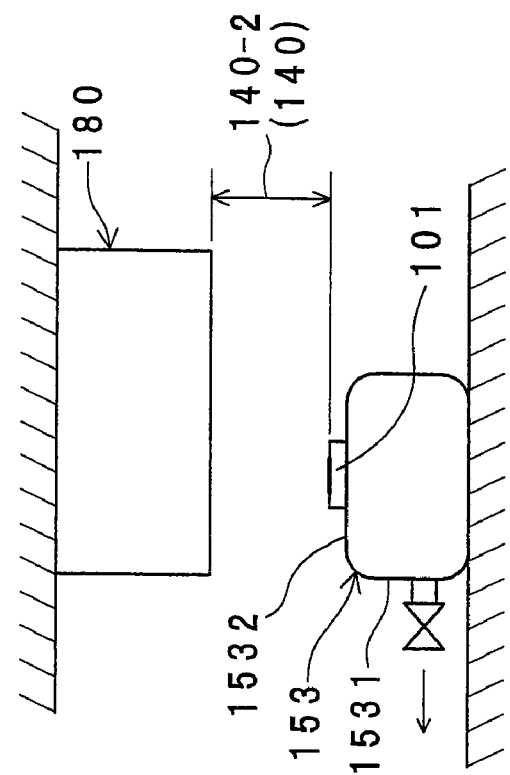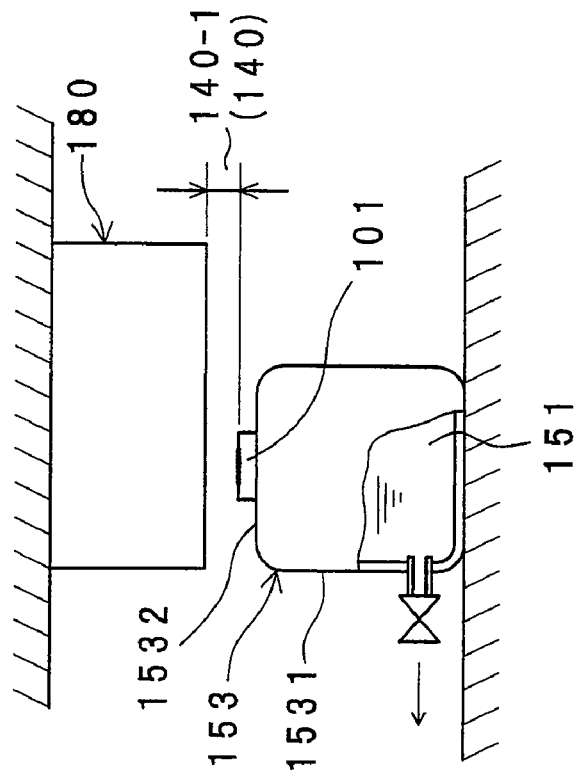

US 7,982,623 B2

RADIO-TYPE TRANSMITTING DEVICE, CONTAINER, TRANSMITTING/RECEIVING SYSTEM AND TRANSMITTING/RECEIVING METHOD

RELATED APPLICATIONS

This application is a Divisional of U.S. application Ser. No. 11/478,845, filed on Jul. 3, 2006 now U.S. Pat. No. 7,821,410, claiming priority of Japanese Patent Application Nos. 2005-195122, filed on Jul. 4, 2005 and 2006-162553, filed on Jun. 12, 2006, the entire contents of each of which are hereby incorporated by reference.

BACKGROUND OF THE INVENTION

1. Field of the Invention

The present invention relates to a radio-type transmitting device which exchanges information with an external transmitting/receiving apparatus without any contact using a radio wave of a radio frequency band, a container including the above radio-type transmitting device, a transmitting/receiving system and a transmitting/receiving method including the above radio-type transmitting device. More specifically, it relates to a radio-type transmitting device, a container, a transmitting/receiving system and a transmitting/receiving method which can manage an amount of contents in the container.

2. Description of the Related Art

Recently, an apparatus which can manage products individually without any contact is being practically used in various fields by having a constitution that each of the products has a tag incorporating an IC chip in which individual information of the product is recorded in an EEPROM. For example, a RFID (Radio Frequency Identification) tag which transmits data and a power without any contact using a radio wave of a radio frequency band in writing/reading information in the EEPROM and supplying a power to the IC chip has come into practical use. In addition, the RFID tag is called a radio tag also and used in various kinds of frequency bands.

As shown in FIG. 19, a RFID tag 10 comprises a transmitting/receiving antenna 12 and the above IC chip 20 on a base member 11. A small RFID tag is a few millimeters in size and 1 gram or less in weight, for example. As shown in FIG. 20, the IC chip 20 comprises a power supply voltage generating unit 21 and a data processing unit 22 when it is functionally divided. The power supply voltage generating unit 21 generates an internal power supply voltage to be used in the data processing unit 22 on the basis of a radio wave of a radio frequency band which is transmitted from an external transmitting/receiving apparatus and received by the antenna 12, and comprises a rectification circuit 23 and a voltage moderation circuit 24 generating a constant voltage. The data processing unit 22 comprises a receive circuit 25 which is connected to the antenna 12 and receives information transmitted from the external transmitting/receiving apparatus, a controller 26 which has a microcomputer for processing the received information to control the RFID tag 10, an information storage unit 27 including an EEPROM for storing individual information as described above, and a send circuit 28 which transmits processed information by the controller 26 to the external transmitting/receiving apparatus through the antenna 12.

It is known in general that propagation of a radio wave in free space is proportional to a transmit power and a receiving sensitivity and inversely proportional to the square of a distance between communications. Therefore, the RFID tag is mounted on a surface of an object to be measured or arranged in the vicinity of the external transmitting/receiving apparatus in order to facilitate the communication. In addition, although there are a transmission method using electromagnetic induction and a transmission method using a microwave in the RFID tag depending on the radio frequency band to be used, the communication distance is determined by a radio power emitted from the external transmitting/receiving apparatus and a radio power emitted from the RFID tag in either case. For example, in a band of 13.56 MHz, a signal and a power are exchanged between loop antennas by electromagnetic induction using coil-shaped loop antennas.

As another communication scheme, load modulation scheme is known. In this scheme, by switching of internal circuits in a RFID tag, the tag makes a load of antenna sent out from an external transmitting/receiving apparatus change instead of the above way sending the radio power from the RFID tag. The load modulation scheme can also obtain effects similar to that of the way sending the radio power.

As the communication distance becomes long, a transmission amount of the power becomes small and the communication cannot be implemented, so a power supply voltage in the RFID tag is lowered. In this case, since information writing error to an internal memory such as the EEPROM might be generated, there is a mechanism in the tag, in which the communication is cut so as to avoid a malfunction when the receive power becomes a predetermined value or less. Meanwhile, when the communication distance is too short, since the transmit power is too high, an excessive voltage is generated in the RFID tag and a defect might be generated. Thus, a circuit restricting the generation of the power supply voltage is also provided in the RFID tag. In general, when a radio wave of a frequency of 13.56 MHz is used, the communication distance is limited in a range from a few centimeters to several tens centimeters depending on specifications of the IC chip and the antenna.

In addition, when a liquid product filled in a container is sold, it is necessary to manage not only characteristic data of the liquid product but also an amount of the contents in many cases. In addition, it is important to manage a remaining amount of the contents while the product is used.

For example, according to a DMFC (Direct Methanol Fuel Cell) in which a power is generated using methanol as a direct fuel, since there are fuel containers containing methanol fuels having various concentrations, in order to appropriately generate a power to provide a maximum output in the fuel cell, it is necessary to supply methanol having an appropriate concentration, that is, about 1 mol %, for example. Thus, for a fuel cell system in which high-concentration methanol solution is supplied and diluted to generate the power, an initial methanol concentration is important information. In this case, when the RFID tag is used, the methanol concentration can be written in its internal memory and the concentration can be easily managed.

In addition, although a power generating operation can be continued semipermanently as long as the fuel is supplied in the fuel cell, the power generation is stopped naturally when the fuel runs out. Therefore, in the fuel cell system, the management of the remaining amount of the fuel is very important. In general, as a method of managing the contents, there is a method of measuring a liquid level using a sensor to estimate the liquid level based on a conductivity or a dielectric constant of the solution, a liquid surface level sensor using reflection of supersonic wave, or the like. However, according to the above method, its cost is high and the number of circuit components for detecting the liquid level is increased, so that the device becomes large and there is a problem in practical use. Therefore, when the fuel cell is used as a power supply for a portable electronic device such as a laptop personal computer, the above sensor cannot be used as a remaining amount detection device of the methanol fuel in the fuel cell.

The above conventional art is disclosed in, for example, Japanese Unexamined Patent Publication No. 9-130999 and Japanese Unexamined Patent Publication No. 6-325229.

As described above, the RFID tag can be appropriately used to manage contents and since the RFID tag itself can be formed in very small size and light in weight, it can be effectively used in a portable electronic device which needs to be small and light.

However, according to the conventional technique using the RFID tag, the RFID tag is arranged within the predetermined transmittable distance so that information is exchanged between the external transmitting/receiving apparatus and the RFID tag as described above. Namely, the external transmitting/receiving apparatus transmits the radio wave with a constant output which corresponds to a communication distance ensuring the predetermined communication distance. Furthermore, according to the conventional technique, only exchanging information to the internal memory is performed between the external transmitting/receiving apparatus and the RFID tag, that is, only information in the internal memory such as the EEPROM and information of a result after the information of the internal memory is processed are communicated.

In other words, according to the conventional technique using the RFID tag, the communication cannot be implemented when the RFID tag exists beyond a set communication range and goes missing. Thus, when the existing position of the RFID tag is unknown, it is out of consideration. Therefore, there has been no proposal to make the external transmitting/receiving apparatus detect the missing RFID tag.

The above Japanese Unexamined Patent Publication No. 6-325229 discloses the communication scheme being able to measure a distance by modulating intervals of response data with reference to a direct voltage obtained by rectifying received radio waves. However in this scheme, since it is necessary to make an interval between response signals even if a lot of intermittent data are sent, communications need waste times. Thus there is a problem that communication efficiency is bad and quick response can not be done.

SUMMARY OF THE INVENTION

The present invention is made to solve the above problems and it is an object of the present invention to provide a radio-type transmitting device corresponding to a RFID tag which can transmit information other than information in its internal memory, a container having the above radio-type transmitting device, a transmitting/receiving system having the above radio-type transmitting device, and a transmitting/receiving method using the above radio-type transmitting device.

In order to accomplish the above object, the present invention is constituted as follows.

That is, a radio-type transmitting device in a first aspect of the present invention, there is provided a radio-type transmitting device comprising:

a power supply voltage generating unit configured to receive a radio wave sent from an external transmitting/receiving apparatus and generate an internal power supply voltage;

a transmission unit configured to transmit information to the external transmitting/receiving apparatus;

an encoding circuit connected to the power supply voltage generating unit and configured to encode receiving sensitivity of the radio wave; and a controller configured to transmit encoded receiving sensitivity information which is encoded by the encoding circuit from the transmission unit to the external transmitting/receiving apparatus.

The controller may include a conversion unit configured to transmit converted information from the transmission unit to the external transmitting/receiving apparatus instead of the receiving sensitivity information, the converted information being information which is different from the receiving sensitivity information, corresponds to the receiving sensitivity information and to which the receiving sensitivity information is converted.

The converted information may be distance information between the external transmitting/receiving apparatus and the radio-type transmitting device, and the conversion unit may include a storage unit configured to store the receiving sensitivity information and the distance information in association with each other, and may be configured to transmit the distance information read from the storage unit from the transmission unit.

The receiving sensitivity information may be a receiving voltage of the received radio wave, and the encoding circuit may be an A/D conversion circuit.

Further, the transmission unit is an antenna and is connected to the controller and the antenna; and may have a load modulation unit configured to modulate an impedance of the antenna in accordance with the receiving sensitivity information by control of the controller.

In the present invention, a radio-type transmitting device in a fifth aspect of the present invention may be designed other than the radio-type transmitting device in the first aspect. In the fifth aspect, there is provided a radio-type transmitting device comprising:

a power supply voltage generating unit configured to receive a radio wave sent from an external transmitting/receiving apparatus and generate an internal power supply voltage;

a transmission unit configured to transmit information to the external transmitting/receiving apparatus;

a communication error detecting circuit configured to detect communication error in a received radio wave; and a controller configured to transmit error information corresponding to the communication error detected by the communication error detecting circuit from the transmission unit to the external transmitting/receiving apparatus.

In the fifth aspect, the radio-type transmitting device may be designed so that the communication error detecting circuit includes a signal intensity changing unit configured to change intensity of the received radio wave and output a received radio wave with changed intensity; and an error determination unit connected to the signal intensity changing unit and configured to detect the communication error in the received radio wave with changed intensity and output a detected communication error to the controller, and the controller is configured to make the intensity of the received radio wave change in the signal intensity changing unit in accordance with the detected communication error.

In the fifth aspect, the radio-type transmitting device may be designed so that, in a case that the external transmitting/receiving apparatus transmits the radio wave having an error correction code, the communication error is an error count detected in error correction, the controller makes the intensity of the received radio wave change in the signal intensity changing unit in accordance with the error count.

In the fifth aspect, the radio-type transmitting device may be designed so that the transmission unit is an antenna and is connected to the controller and the antenna; and has a load modulation unit configured to modulate an impedance of the antenna in accordance with the error information by control of the controller.

In addition, a container according to a second aspect of the present invention comprises an outer container configured to contain contents which vary in quantity, and either the radio-type transmitting device in the first aspect or the radio-type transmitting device in the fifth aspect.

According to the second aspect, the contents is liquid and the radio-type transmitting device may include a base member with which the radio-type transmitting device floats on a surface of the liquid and is arranged in the outer container.

According to the second aspect, the container may be designed so that the outer container is made of a flexible material so that a shape of the outer container is varied in accordance with an amount of the contents, and the radio-type transmitting device is mounted on a surface of the outer container.

According to the second aspect, the container may be designed so that a partition member that is provided in the outer container and is movable in the outer container in accordance with the amount of the contents may be further included, and the radio-type transmitting device may be mounted on the partition member.

In addition, according to a transmitting/receiving system according to a third aspect of the present invention comprises either the radio-type transmitting device according to the first aspect or the radio-type transmitting device according to the fifth aspect and an external transmitting/receiving apparatus exchanging information wirelessly with the radio-type transmitting device.

According to the third aspect, the transmitting/receiving system may be designed so that the external transmitting/receiving apparatus includes a transmitting/receiving unit configured to transmit a radio wave to the radio-type transmitting device and receive the receiving sensitivity information transmitted from the transmission unit of the radio-type transmitting device or distance information between the external transmitting/receiving apparatus and the radio-type transmitting device.

According to the third aspect, the transmitting/receiving system may be designed so that, in a case that the radio-type transmitting device transmits the receiving sensitivity information, the external transmitting/receiving apparatus further includes a distance determination unit configured to be connected to the transmitting/receiving unit and obtain the distance information between the external transmitting/receiving apparatus and the radio-type transmitting device in accordance with the receiving sensitivity information.

According to the third aspect, the transmitting/receiving system may be designed so that the distance determination unit includes a transmitting device storage unit configured to store the receiving sensitivity information and the distance information in association with each other; and a reading unit configured to read the distance information corresponding to the receiving sensitivity information received at the transmitting/receiving unit.

According to the third aspect, a container containing contents which vary in quantity and in which the radio-type transmitting device is disposed may be further included.

According to the third aspect, the contents is liquid and the radio-type transmitting device may include a base member with which the radio-type transmitting device floats on a surface of the liquid and is arranged in the container.

According to the third aspect, the transmitting/receiving system may be designed so that the container is made of a flexible material so that an outer shape of the container is varied in accordance with variation of the amount of the contents, and the radio-type transmitting device is mounted on a surface of the container.

According to the third aspect, the radio-type transmitting device may be mounted on a partition member which is provided in the container and is movable in the outer container in accordance with the amount of the contents.

According to the third aspect, the contents may be methanol solution for a fuel cell and the container may be a fuel tank capable of connecting to a direct methanol fuel cell system.

In the third aspect, the contents may be infusion and the container may be an infusion container containing the infusion therein.

In the third aspect, the transmitting/receiving system may be designed so that the contents are printing papers, and the container is a sheet tray containing the printing papers, the sheet tray has a paper feeding mechanism configured to load the printing papers, to be movable within the sheet tray in accordance with variation of the amount of the printing papers, and to attach the radio-type transmitting device.

In the third aspect, the contents may be ink, and the container may be an ink cartridge containing the ink therein.

According to the third aspect, the transmitting/receiving system may be designed so that the radio-type transmitting device includes an information storage unit configured to store management information which is information relating to at least one of the contents and the container and is transmitted from the transmission unit of the radio-type transmitting device to the external transmitting/receiving apparatus.

According to the third aspect, the transmitting/receiving system may be designed so that the management information relating to the contents shows a kind of the contents, and the management information relating to the container shows at least one of a manufacturing date and a use history of the container.

In the third aspect, the transmitting/receiving system may be designed so that the radio-type transmitting device includes an information storage unit configured to store management information which is information relating to at least one of the contents and the container and is transmitted from the transmission unit of the radio-type transmitting device to the external transmitting/receiving apparatus; the management information relating to the contents shows a kind of the contents, and the management information relating to the container shows at least one of a manufacturing date and a use history of the container; and the external transmitting/receiving apparatus has a display unit for displaying the management information.

In addition, a transmitting/receiving method according to a fourth aspect of the present invention comprising: receiving a radio wave transmitted from an external transmitting/receiving apparatus at a radio-type transmitting device to generate an internal power supply voltage;

transmitting information from the radio-type transmitting device to the external transmitting/receiving apparatus;

after generating the internal power supply voltage before transmitting information, encoding receiving sensitivity of the radio wave; and transmitting an encoded receiving sensitivity information to the external transmitting/receiving apparatus.

According to the fourth aspect, the transmitting/receiving method may be designed so that the receiving sensitivity information is a receiving voltage of the received radio wave, and the method further comprising:

obtaining distance information between the external transmitting/receiving apparatus and the radio-type transmitting device in accordance with the receiving sensitivity information; and transmitting the distance information to the external transmitting/receiving apparatus instead of the receiving sensitivity information.

According to a fourth aspect, the transmitting/receiving method may be designed so that the radio-type transmitting device is disposed in the container containing contents which vary in quantity, and the distance information corresponds to the amount of the contents in the container.

In the fourth aspect, the transmitting/receiving method may be designed so that the radio wave transmitted from the radio-type transmitting device to the external transmitting/receiving apparatus is modulated in accordance with the receiving sensitivity information and then transmitted.

In the present invention, a transmitting/receiving method in a sixth aspect of the present invention may be designed other than the transmitting/receiving method in the fourth aspect. In the sixth aspect, there is provided a transmitting/receiving method comprising:

receiving a radio wave transmitted from an external transmitting/receiving apparatus at a radio-type transmitting device to generate an internal power supply voltage;

transmitting information from the radio-type transmitting device to the external transmitting/receiving apparatus;

after generating the internal power supply voltage before transmitting information, detecting communication error in the radio wave transmitted from the external transmitting/receiving apparatus by the radio-type transmitting device; and transmitting error information corresponding to a detected communication error from the radio-type transmitting device to the external transmitting/receiving apparatus.

In the sixth aspect, the transmitting/receiving method may be designed so that, when it is difficult to detect the communication error, the radio-type transmitting device changes intensity of receiving signal of the radio wave so as to be able to detect the communication error.

In the sixth aspect, the transmitting/receiving method may be designed so that, when the external transmitting/receiving apparatus transmits the radio wave having an error correction code, the communication error is an error count detected in error correction, the radio-type transmitting device changes intensity of receiving signal in accordance with the error count.

In the sixth aspect, the transmitting/receiving method may be designed so that the radio wave transmitted from the radio-type transmitting device to the external transmitting/receiving apparatus is modulated in accordance with the error information and then transmitted.

According to the radio-type transmitting device in the first aspect, since it comprises the encoding circuit and the controller, even when the external transmitting/receiving apparatus transmitting the radio wave to the radio-type transmitting device transmits the radio wave with the constant output like before, the radio-type transmitting device can transmit the receiving sensitivity information to the external transmitting/receiving apparatus depending on intensity of the receiving sensitivity in the radio-type transmitting device, that is, depending on the distance between the external transmitting/receiving apparatus and the radio-type transmitting device. Therefore, since the information other than the information in the internal memory in the radio-type transmitting device can be transmitted, new information, that is, distance information, for example can be provided. Thus, as one application, the radio-type transmitting device can be used for managing a remaining amount of the contents in the container.

In addition, the receiving sensitivity information may be converted to the distance information and the distance information may be transmitted.

Since the radio-type transmitting device is as small as a few millimeters square in size and light in weight, it can be appropriately used as a device to measure a remaining amount of a fuel in the direct methanol fuel cell system for the portable electronic device, for example.

Further, according to the radio-type transmitting device in the fifth aspect, since the communication error detecting circuit and controller are provided, communication error information corresponding to communication error at the radio-type transmitting device can be sent to the external transmitting/receiving apparatus. Thus, since the information other than the information in the internal memory in the radio-type transmitting device can be transmitted, new information, that is, distance information, for example can be provided.

Also, the so-called load modulation scheme can be adopted in the radio-type transmitting devices of the first and fifth aspects. According to adopting the load modulation scheme, the power for transmission from the radio-type transmitting device can be reduced.

Furthermore, according to the container in the second aspect, since it has the radio-type transmitting device in the first or fifth aspect, the container in which the management of the remaining amount of the contents can be done in the constitution of the small in size and light in weight can be provided. Therefore, the container is effectively used as a fuel tank in the direct methanol fuel cell system for the portable electronic device, for example.

Still furthermore, according to the transmitting/receiving system in the third aspect, since both have the radio-type transmitting device in the first or fifth aspect, new information other than the information in the internal memory of the radio-type transmitting device, that is, receiving sensitivity information of the radio wave can be transmitted.

When the radio-type transmitting device transmits the receiving sensitivity information, since the external transmitting/receiving apparatus comprises the distance determination unit, the distance information between the external transmitting/receiving apparatus and the radio-type transmitting device can be obtained. As one example the distance information is used, the transmitting/receiving system can be a system of managing the remaining amount of the contents. Especially, the transmitting/receiving system is effectively used for managing the remaining amount of the fuel in the direct methanol fuel cell system for the portable electronic device which requires very small device constitution, for example. Furthermore, according to the transmitting/receiving system, the information of the internal memory in the radio-type transmitting device such as a property value and the like of the contents can be transmitted, so that not only the amount of the contents but also the contents and the container can be managed.

Also, according to the transmitting/receiving method in the fourth aspect, since the receiving sensitivity is encoded in the radio-type transmitting device and then sent to the external transmitting/receiving apparatus, new information other than the information in the internal memory in the radio-type transmitting device, for example distance information, can be transmitted to the external transmitting/receiving apparatus.

Also, according to the transmitting/receiving method in the sixth aspect, since the communication error information corresponding to communication error at the radio-type transmitting device is transmitted to the external transmitting/receiving apparatus, new information other than the information in the internal memory in the radio-type transmitting device, for example distance information, can be transmitted to the external transmitting/receiving apparatus.

BRIEF DESCRIPTION OF THE DRAWINGS

These and other aspects and features of the present invention will become clear from the following description taken in conjunction with the preferred embodiments thereof with reference to the accompanying drawings, in which:

FIG. 6A is a view showing a constitution of a transmitting/receiving system including the radio-type transmitting device shown in FIG. 1 according to the embodiment of the present invention, and shows that contents in a container is sufficient;

FIG. 6B is a view showing a constitution of a transmitting/receiving system including the radio-type transmitting device shown in FIG. 1 according to the embodiment of the present invention, and shows that contents is scarce;

FIG. 7A is view showing another example of the transmitting/receiving system according to the embodiment of the present invention, and shows that contents in a container is sufficient;

FIG. 7B is view showing another example of the transmitting/receiving system according to the embodiment of the present invention, and shows that contents is scarce;

DETAILED DESCRIPTION OF THE PREFERRED EMBODIMENTS

Figure 1:
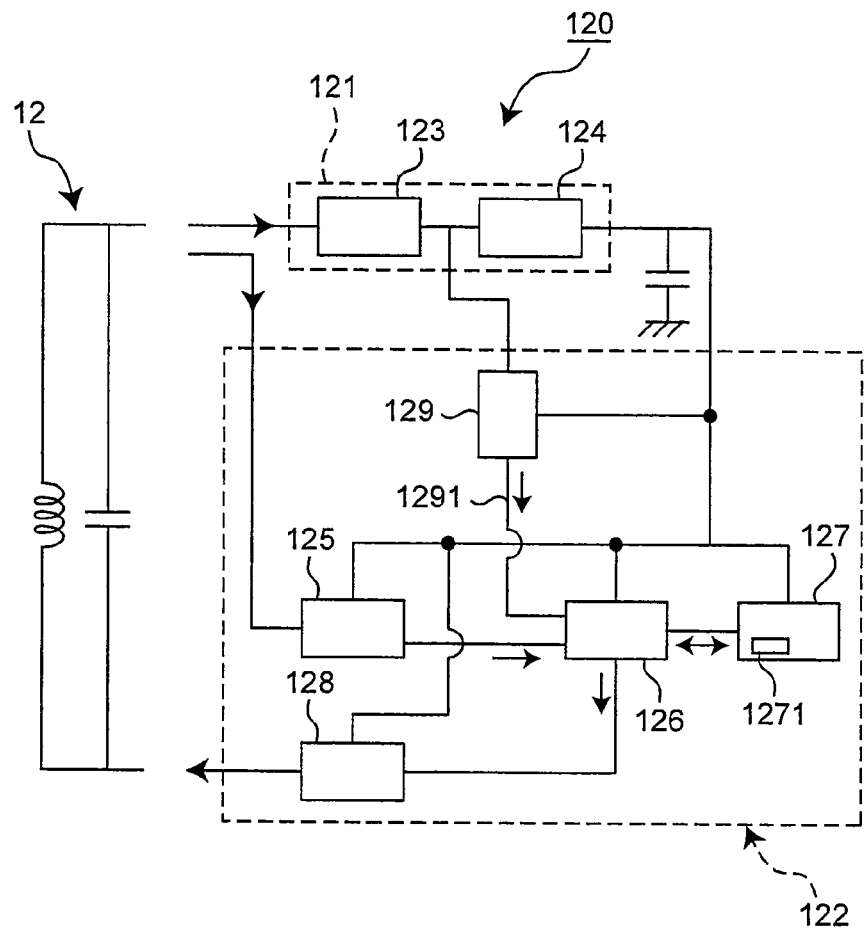
FIG. 1 is a block diagram showing a constitution of a radio-type transmitting device according to an embodiment of the present invention.

Descriptions will be made of a radio-type transmitting device according to an embodiment of the present invention, a container having the above radio-type transmitting device, a transmitting/receiving system having the above radio-type transmitting device, and a transmitting/receiving method using the above radio-type transmitting device in detail with reference to the drawings. In addition, the same reference numerals are allotted to the same components in the drawings.

Figure 8:
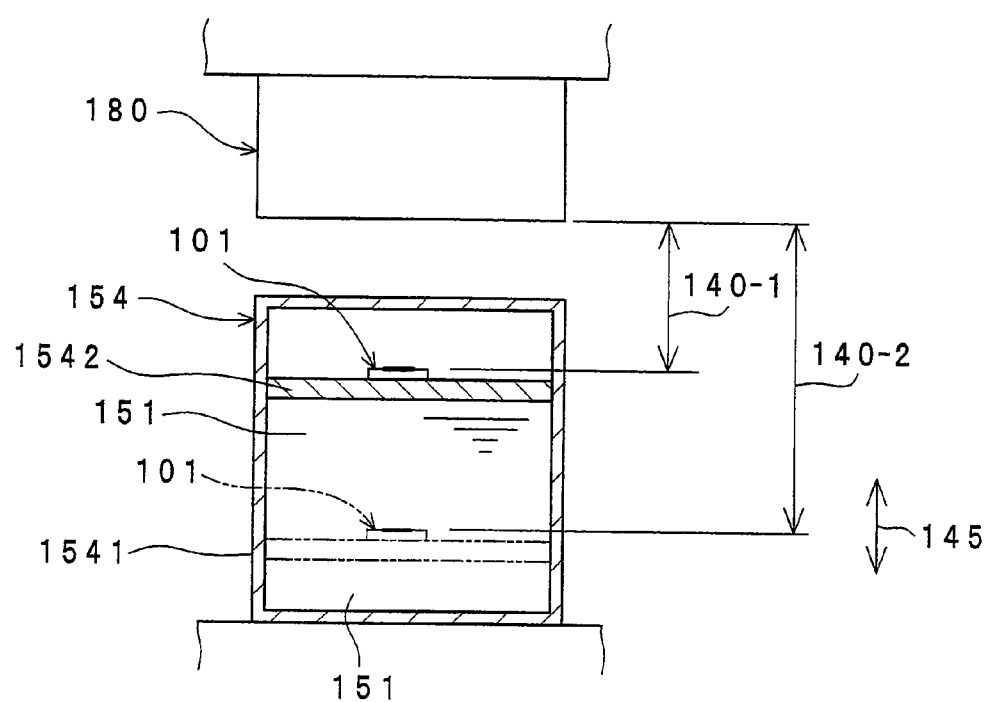
FIG. 8 is a view showing another example of the transmitting/receiving system according to the embodiment of the present invention.

In addition, although a RFID (Radio Frequency Identification) tag is used as an example of the radio-type transmitting device in this embodiment, the present invention is not limited to this. In addition, as the transmitting/receiving system including the radio-type transmitting device and the transmitting/receiving method performed in that transmitting/receiving system, a DMFC (Direct Methanol Fuel Cell) which can be mounted on a portable electronic equipment such as a notebook PC, for example and can supply a power to the portable electronic equipment is taken as an example. The present invention, however, is not limited to this and they can be used in a system using information regarding receiving sensitivity in the radio-type transmitting device within a scope easily conceived by those skilled in the art. For example, they can be used when liquid is stored, that is, a case a petroleum fuel such as kerosene or gasoline is stored in a container, a case a remaining amount of the gasoline stored in a fuel tank of a car is managed, a case a seasoning material, oil, soup, and liquor are stored in a container or an apparatus from which the seasoning material and so on are supplied, and the like. In addition, they can be used in a large size container such as a storage tank for crude oil having a floating lid. Furthermore, they can be used for storing a solid such as a rice bin and the like in a case other than the contents of liquid. In this case, configurations shown in FIGS. 7A, 7B and 8 are preferable, for example. In addition, the configurations shown in FIGS. 7A, 7B and 8 may be used when the contents are gas. Similarly, although the liquid level meter for the methanol solution for the fuel cell is illustrated as an object to be managed using the radio-type transmitting device in this embodiment, the present invention is not limited to this of course.

First Embodiment

First, a radio-type transmitting device according to this embodiment will be described.

Figure 3:
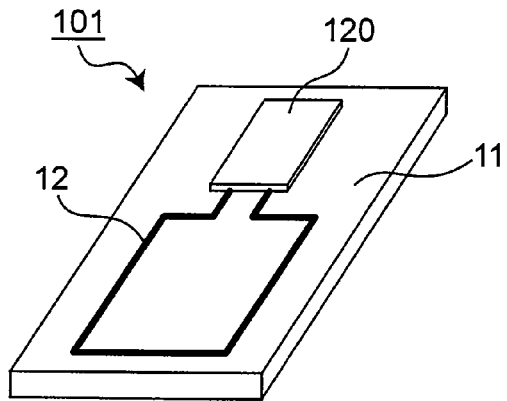
FIG. 3 is a perspective view showing the radio-type transmitting device shown in FIG. 1.

As described above, as the radio-type transmitting device, a RFID tag 101 shown in FIG. 3 is taken as an example. According to the RFID tag 101, an antenna 12 for transmitting and receiving radio wave such as a loop-shaped and an IC chip 120 are provided on a base member 11, which is about a few millimeters square, for example. As will be described below, when the RFID tag 101 is floated on a liquid surface of a methanol solution in a container such as a fuel tank, the base member 11 is made of a material having a density or specific gravity smaller than that of the liquid on which the base member 11 is to be floated. In addition, since the base member 11 has only to be floated on a liquid surface, a density of the base member 11 is not necessarily smaller than that of the liquid and it may be greater than that of the liquid as long as the base member 11 can be floated on the liquid surface by surface tension. In addition, when waterproof or water repellent treatment is performed on an entire surface of the RFID tag, a circuit of the antenna 12 and IC chip 120 can be protected and a more stable floating property can be provided.

As shown in FIG. 1, the IC chip 120 comprises a power supply voltage generating unit 121 and a data processing unit 122 when it is functionally divided. The power supply voltage generating unit 121 generates an internal power supply voltage to be used in the data processing unit 122 on the basis of a radio wave of a radio frequency band which is transmitted from an external transmitting/receiving apparatus and received by the antenna 12, and comprises a rectification circuit 123 and a voltage moderation circuit 124. In addition, the external transmitting/receiving apparatus communicates with the RFID tag 101 as will be described below. The rectification circuit 123 rectifies a carrier signal of the radio wave and converts it to a DC voltage. The voltage moderation circuit 124 generates a constant voltage to control the DC voltage generated by the rectification circuit 123 which is varied with intensity of the received radio wave. Namely, the voltage moderation circuit 124 restricts the output DC voltage of the rectification circuit 123 when it is too high, and cut it at a specific lower limit value when it is too low. The above constant voltage is supplied to each component of the data processing unit 122 as an operation power supply.

The data processing unit 122 comprises a receive circuit 125 which is connected to the antenna 12 and extracts information from the received radio wave outputted from the external transmitting/receiving apparatus, a controller 126 has a microcomputer for processing the received information and controls the RFID tag 101, an information storage unit 127 including an EEPROM for storing information, and a send circuit 128 which transmits information processed in the controller 126 to the external transmitting/receiving apparatus through the antenna 12, and further comprises an encoding circuit 129 which is a new constitution and does not exist in the conventional example. In addition, the send circuit 128 and the antenna 12 function as a transmission unit.

The encoding circuit 129 is connected to the rectification circuit 123, detects the receiving sensitivity of the radio wave received at the antenna 12, and digitalizes receiving sensitivity information, specifically, a receiving voltage, in other words, the output voltage of the rectification circuit 123 in this embodiment. The encoding circuit 129, in this embodiment, transmits a digitalized receiving sensitivity information 1291 to the controller 126. Such encoding circuit 129 may comprise an A/D conversion circuit or a constitution in which a frequency is counted by using a voltage counting circuit (VCO). The output form of the encoding circuit 129 is not limited to the above digitalizing form and can be adopted a number of forms in correspondence to the detection of the receiving sensitivity. For example, the forms of textual information and pictorial information can be used.

The controller 126 executes a certain command supplied from the receive circuit 125, so that when data is to be written, the controller 126 writes the result for execution of the command to the information storage unit 127 and when data is to be read out, the controller 126 reads the data from the information storage unit 127 and sends the data from the loop antenna 12 through the send circuit 128. For example, when a command to send fuel data stored in the information storage unit 127 is transmitted, the controller 126 reads out the data in the information storage unit 127 such as methanol concentration numeric data and supplies a power as a radio wave modulated to the radio frequency band by the send circuit 128 to the loop antenna 12 to send the data. In addition, management information 1271 regarding at least one of contents and a container of the contents is stored in the information storage unit 127 other than the concentration data. The management information 1271 regarding the contents includes information showing a kind of the contents, for example, and the management information 1271 regarding the container includes information showing at least one of a manufacturing date and a use history of the container, for example. At the time of reading, at least one of those information is read out.

According to the RFID tag 101 in this embodiment, the controller 126 performs sending control in which the receiving sensitivity information 1291 supplied from the encoding circuit 129 is modulated to the radio frequency band by the send circuit 128 and supplied to the loop antenna 12 as the radio wave.

Figure 4:
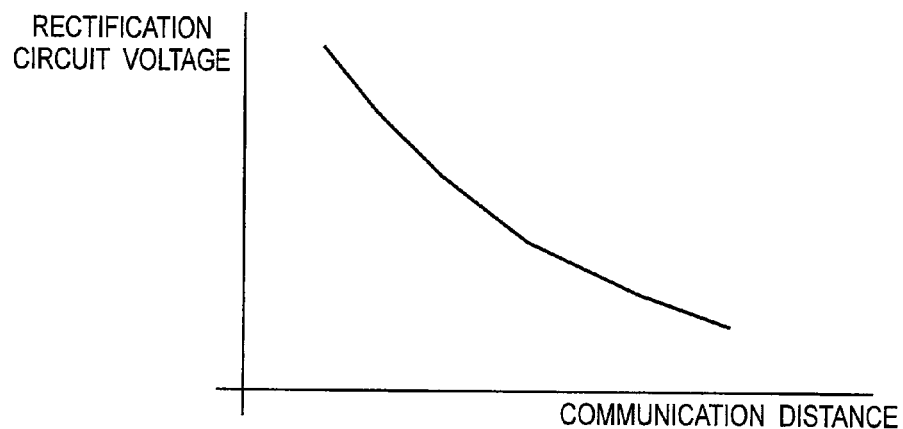
FIG. 4 is a graph showing a schematic relation between an output voltage of a rectification circuit shown in FIG. 1 and a communication distance.
Figure 5:
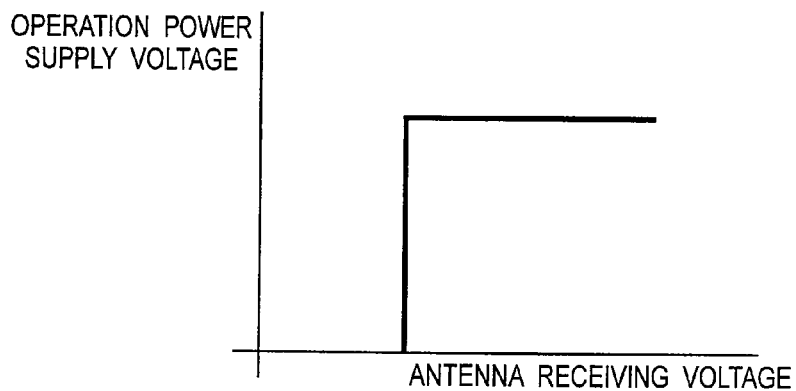
FIG. 5 is a graph showing a relation between a receiving voltage in the radio-type transmitting device shown in FIG. 1 and an operation power supply voltage.

More specifically, although the receive power in the antenna 12 is related to a transmit power, transmit sensitivity, and the receiving sensitivity, the receive power largely depends on a distance between the external transmitting/receiving apparatus and the RFID tag 101 as shown in a relation between an output voltage of the rectification circuit 123 which is varied with the receiving sensitivity and a communication distance in FIG. 4. As described above, only when the distance between the external transmitting/receiving apparatus and the RFID tag 101 is shorter than a predetermined distance, both can communicate with each other due to characteristics of the voltage moderation circuit 124. That is, as shown in FIG. 5, only when the antenna receiving voltage is more than a predetermined threshold input level, a constant operation power supply voltage is generated form the voltage moderation circuit 124. In other words, the distance between the RFID tag 101 and the external transmitting/receiving apparatus can be estimated by a receiving power value in the RFID tag 101. That is, this can be used as a liquid-level meter of the liquid in the container. Thus, according to this embodiment, it is so constituted that the receiving power in the RFID tag 101 is digitalized in the encoding circuit 129 and the digital value is sent to the external transmitting/receiving apparatus.

Figure 2:
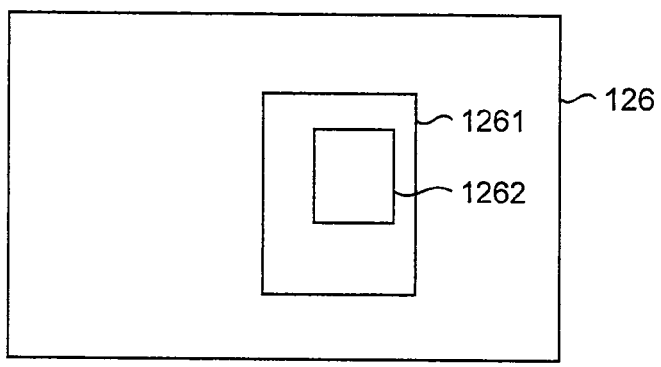
FIG. 2 is a block diagram showing a constitution of a controller shown in FIG. 1.

In addition, according to the RFID tag 101 in this embodiment, although the digitalized receiving sensitivity information 1291 is returned to the external transmitting/receiving apparatus as described above, the following can be also constituted. That is, the controller 126 has a conversion unit 1261 as shown in FIG. 2. The conversion unit 1261 transmits converted information which corresponds to the receiving sensitivity information 1291 but different from the receiving sensitivity information and to which the receiving sensitivity information is converted from the send circuit 128 to the external transmitting/receiving apparatus instead of the receiving sensitivity information 1291. The converted information is, for example, distance information between the external transmitting/receiving apparatus and the RFID tag 101. The conversion unit 1261 may calculate the converted information based on the receiving sensitivity information 1291 using a given arithmetic expression, or may read the converted information from a table in which the receiving sensitivity information 1291 and the converted information are associated with each other. The table is previously stored in a storage unit 1262 included in the conversion unit 1261 and the converted information read from the storage unit 1262 may be transmitted from the send circuit 128.

A transmitting/receiving system 190 shown in FIGS. 6A and 6B including the external transmitting/receiving apparatus 180 and the RFID tag 101 is taken as an example and will be described as an application of the RFID tag 101 having the above constitution. In addition, an object to be managed in the transmitting/receiving system 190 is a remaining amount of liquid, that is, a liquid level.

The RFID tag 101 is floated on a liquid surface 151*a* of liquid 151 in the container 150. FIG. 6A shows a state the container 150 is filled with the liquid 151 and a distance between the external transmitting/receiving apparatus 180 and the RFID tag 101 is a distance 140-1 and a remaining amount of the liquid 151 is a remaining amount 155-1. Meanwhile, FIG. 6B shows a state the liquid 151 is used and its level is low, and a distance between the external transmitting/receiving apparatus 180 and the RFID tag 101 is a distance 140-2 and a remaining amount of the liquid 151 is a remaining amount 155-2. In addition, the above distances 140-1 and 140-2 may be collectively referred to as distance information 140 between the external transmitting/receiving apparatus 180 and the RFID tag 101 occasionally, and the above remaining amounts 155-1 and 155-2 may be collectively referred to as a remaining amount 150 of the liquid 151 occasionally.

The external transmitting/receiving apparatus 180 is arranged so as not to come in contact with the RFID tag 101 and it wirelessly communicates with the RFID tag 101 to exchange information. The external transmitting/receiving apparatus 180 comprises a transmitting/receiving unit 160 and a transmitting device controller 170. The transmitting/receiving unit 160 comprises a loop-shaped antenna 161 serving as an input/output terminal for electromagnetic induction which communicates with the antenna 12 of the RFID tag 101, and a transmitting/receiving circuit 162 for the electromagnetic induction. The transmitting/receiving unit 160 transmits the radio wave to the RFID tag 101 and receives the receiving sensitivity information 1291 or the distance information 140 between the external transmitting/receiving apparatus 180 and the RFID tag 101 transmitted from the RFID tag 101. The transmitting device controller 170 is a unit to control the external transmitting/receiving apparatus 180.

In addition, since the external transmitting/receiving apparatus 180 is arranged on the side of an apparatus, a relatively large scale circuit can be applicable.

According to this embodiment, the RFID tag 101 returns the receiving voltage information as the receiving sensitivity information 1291 as describe above. Therefore, the transmitting device controller 170 of the external transmitting/receiving apparatus 180 comprises a distance determination unit 171 which obtains the distance information 140 between the external transmitting/receiving apparatus 180 and the RFID tag 101 according to the receiving sensitivity information 1291. The distance determination unit 171 may calculate the distance information 140 based on the receiving sensitivity information 1291 using a given arithmetic expression, or may read the distance information 140 from a table in which the receiving sensitivity information 1291 and the distance information 140 are associated with each other. The table is previously stored in a transmitting device storage unit 1711 included in the distance determination unit 171. The distance information 140 is read from the transmitting device storage unit 1711 by a reading unit 1712.

The obtained distance information 140 is transmitted from the transmitting device controller 170.

In addition, in a case that the distance information 140 is transmitted from the RFID tag 101, the transmitting device controller 170 transmits the distance information 140 which is received by the transmitting/receiving unit 160 and supplied to the controller 170.

The transmitting device controller 170 may be connected to a display device 185 which displays the liquid level visibly, so that the transmitting/receiving system 190 may constitute a liquid-level meter, or may transmit the distance information 140 to a high-level control unit as will be described below.

A transmitting/receiving method in the transmitting/receiving system 190 having the above constitution will be described.

In a basic operation of the transmitting/receiving, the transmitting device controller 170 controls the transmitting/receiving unit 160 so that transmission is made at a predetermined output voltage. When the RFID tag 101 receives the radio wave of the predetermined constant output voltage and it is in a transmittable position, the internal voltage is generated based on the received radio wave and the receiving sensitivity is encoded, that is, in this embodiment, the output voltage of the rectification circuit 123 is digitalized as described above. In addition, data is written in the information storage unit 127 or data is read from the information storage unit 127 in some cases. Thus, the digitalized receiving voltage information 1291 or the distance information 140 which was converted based on the receiving voltage information 1291 is transmitted from the RFID tag 101 to the transmitting device controller 170.

As shown in FIG. 6A, when the container 150 is filled with the liquid 151, the RFID tag 101 is floated on the liquid surface 151*a* and the distance 140 from the antenna 161 of the external transmitting/receiving apparatus 180 is the distance 140-1. In this communication distance 140-1, the communication between the external transmitting/receiving apparatus 180 and the RFID tag 101 can be implemented enough, the power received at the RFID tag 101 is high and the DC voltage of the output of the rectification circuit 123 is also high.

Meanwhile, as shown in FIG. 6B, when the liquid 151 in the container 150 is used and the distance 140 from the antenna 161 of the external transmitting/receiving apparatus 180 becomes the distance 140-2, the communication distance becomes long. At this time, the voltage for electromagnetic induction at the antenna 12 of the RFID tag 101 becomes low and finally becomes lower than the threshold level of the input voltage of the voltage modification circuit 124. Thus, the power cannot be supplied to the RFID tag 101. When the power cannot be supplied to the RFID tag 101, the RFID tag 101 cannot return the receiving voltage information 1291 or the distance information 140. Thus, since the external transmitting/receiving apparatus 180 does not receive the return from the RFID tag 101, it is determined that the liquid 151 is reduced below a predetermined level or the container 150 itself does not exist.

In addition, a limit distance of the communication can be specified by setting a power supply voltage to the voltage modification circuit 124.

Although it is detected that the liquid 151 is reduced below the predetermined level when no transmission is performed from the RFID tag 101 in the above embodiment, there may be another constitution such that the receiving voltage information 1291 or the distance information 140 is transmitted from the RFID tag 101 even when the liquid 151 in the container 150 runs down. Its embodiment will be described hereinafter.

For example, the external transmitting/receiving apparatus 180 transmits a command signal which is modulated at a frequency of 13.56 MHz to the RFID tag 101 at 30 mW, for example. When the distance 140 between the loop antenna 161 of the external transmitting/receiving apparatus 180 and the loop antenna 12 of the RFID tag 101 is 15 mm, the DC voltage taken out at the rectification circuit 123 by a carrier component of 13.56 MHz is 6.2 V. In addition, when the distance 140 between the loop antenna 161 of the external transmitting/receiving apparatus 180 and the loop antenna 12 of the RFID tag 101 is 30 mm, the DC voltage taken out at the rectification circuit 123 by the carrier component of 13.56 MHz is 1.5 V. It is to be noted that the above values are examples in this embodiment.

Thus, when the distance 140 between the loop antennas is varied, the DC voltage value from the rectification circuit 123 is varied and the controller 126 of the RFID tag 101 stores the DV voltage value supplied from the encoding circuit 129 and when the external transmitting/receiving apparatus 180 requests the return, this voltage value is sent.

Since the receive power of the RFID tag 101 is proportional to the transmit power of the external transmitting/receiving apparatus 180 and almost inversely proportional to the square of the communication distance 140, the distance 140 between the antenna 161 of the external transmitting/receiving apparatus 180 and the antenna 12 of the RFID tag 101 can be easily estimated. Thus, the liquid level can be also estimated. In practical use, in order to reduce an error factor such as reflection of the received radio wave in the vicinity of the RFID tag 101, it is preferable to use an evaluation table showing a relation between an amount of the liquid 151 in the container 150 and the DC voltage value supplied from the encoding circuit 129.

According to the above transmitting/receiving system 190, an outer container 152 of the container 150 is not deformed, and the liquid 151 is varied in the container 150 and the RFID tag 101 is floated on the liquid surface 151*a* of the liquid 151. In another case, the following constitution shown in FIGS. 7A and 7B may be also provided.

According to a transmitting/receiving system shown in FIGS. 7A and 7B, an outer container 1531 of a container 153 is made of an elastic material such as a rubber so that its shape is varied with the variations of the amount of the contents such as liquid 1511. Thus, a height of the outer container 1531 is varied with the amount of the liquid 151. Thus, when the RFID tag 101 is mounted on a surface 1532 of the outer container 1531 which is opposed to the external transmitting/receiving apparatus 180, the variation of the distance 140 between the external transmitting/receiving apparatus 180 and the RFID tag 101 can be detected as the increase and decrease of the amount of the contents. FIG. 7A shows a state the outer container 1531 is filled with the liquid 151 and FIG. 7B shows a state the liquid 151 in the outer container is reduced.

In addition, the entire outer container 1531 may be made of the same material or the outer container 1531 may be partially made of a different material. For example, it is preferable for the measurement that the opposed surface 1532 keeps state almost parallel to the external transmitting/receiving apparatus 180 regardless of the variation of the outer container 1531 in height. Thus, it may be designed so that the state of deformation of the container 153 varies from place to place, for example, the opposed surface 1532 may be made of a hard material which is not likely deformed. Thus, even when a posture of the container 153 is varied, since the distance information 140 is constant, the variation of the amount of the contents can be measured with high precision.

In addition, a constitution shown in FIG. 8 may be employed. According to a transmitting/receiving system shown in FIG. 8, an outer container 1541 of a container 154 is not deformed but a partition member 1542 which can be moved along a Z-axis direction 145 shown in the Figure corresponding to a vertical direction in the outer container 1541 is provided. Liquid 151 as one example of contents is squeezed outward from the outer container 1541 as the partition member 1542 is moved along an inner wall of the outer container 1541. Thus, the partition member 1542 is moved in accordance with the variation of the amount of the liquid 151. Therefore, by a constitution that the external transmitting/receiving apparatus 180 is arranged to be opposed to the partition member 1542 and the RFID tag 101 is mounted on the partition member 1542, variation of the distance 140 between the external transmitting/receiving apparatus 180 and the RFID tag 101 can be detected from the increase and decrease of the contents. In addition, by ensuring the hermeticity between the partition member 1542 and the outer container 1541, the liquid 151 can be prevented from being leaked outside or air can be prevented from entering into the outer container 1541 even when a posture of the container 154 is varied. In this case, since the partition member 1542 is moved only in the Z-axis direction 145, even when the posture of the container 154 is varied, the distance information 140 is constant, so that the variation of the amount of the contents can be measured with high precision.

In addition, the constitution of the transmitting/receiving system is not limited to the above, and transmitting/receiving systems can be constituted within a scope easily conceived by those skilled in the art.

Figure 9:
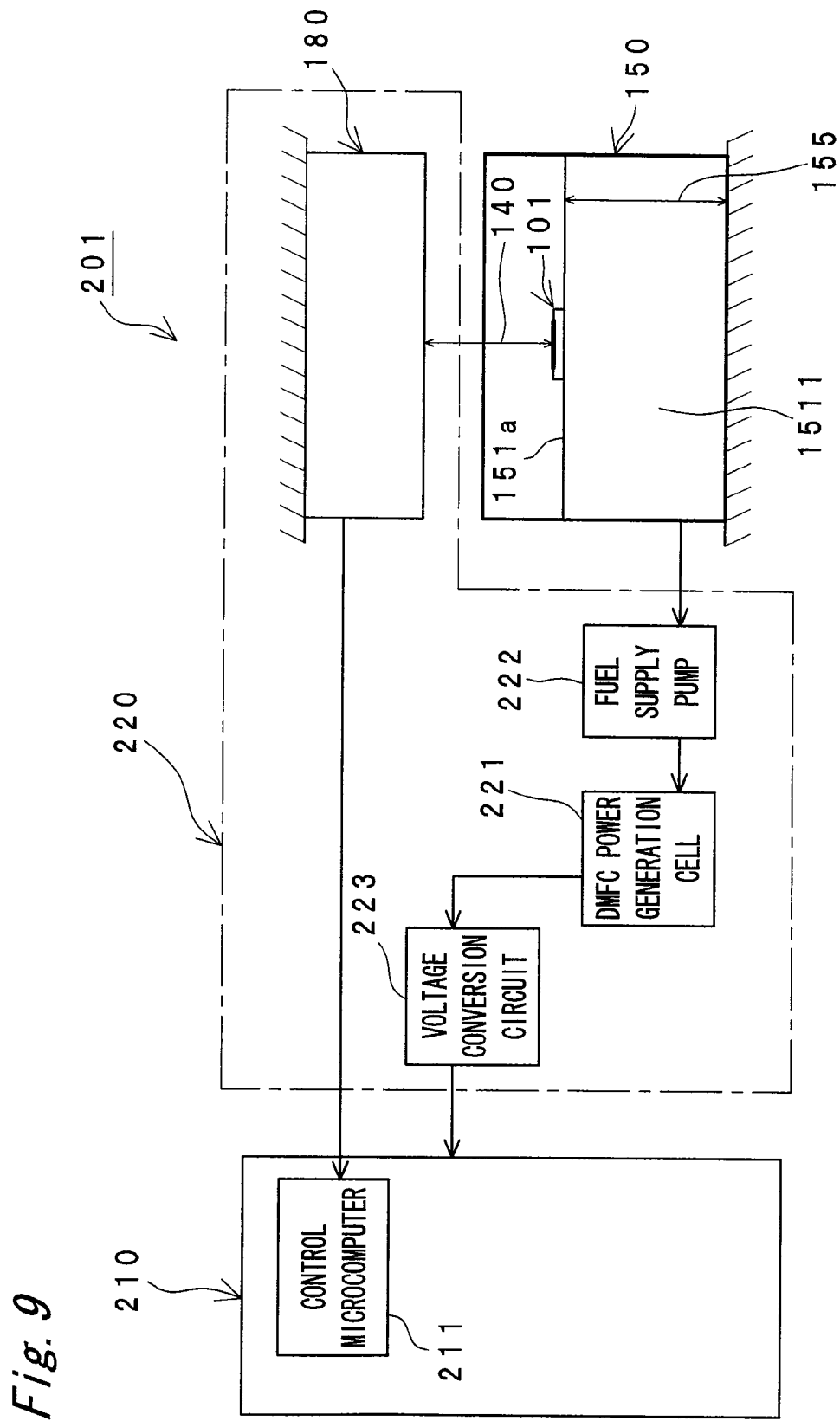
FIG. 9 is a view showing an example of a system including the transmitting/receiving system shown in FIGS. 6A and 6B.

FIG. 9 shows an example of an application system including the above-described transmitting/receiving system 190 and the like. According to an application system 201 shown in FIG. 9, a direct methanol fuel cell unit 220 is used as one of the power supplies in an electronic apparatus 210, and the transmitting/receiving system 190 is used for management of a remaining amount of the methanol solution 1511 in the fuel container 150 provided in the fuel cell unit 220. Here, the electronic apparatus 210 corresponds to a portable electronic device such as a notebook personal computer, etc. In addition, the container 150 containing the methanol solution 1511 is detachable from the fuel cell unit 220. In addition, the methanol solution 1511 includes not only an undiluted methanol solution but also a methanol solution whose concentration is appropriately adjusted for the generation of electricity. Also, although the methanol is taken as an example of the fuel, the fuel is not limited to the methanol. For example, liquid made by dissolving borohydride in alkali solution can be used as the fuel.

As described above, since the IC chip 120 can be manufactured in a minute size, the RFID tag 101 also can be manufactured into a size of a few millimeters square. Therefore, it is not too much to say that the RFID tag 101 makes it possible to be mounted on the small size fuel container 150 mounted on the portable electronic device 210 to detect the contents of the container 150 for the first time. In addition, since the RFID tag 101 is light in weight, even when the RFID tag 101 is attached on the upper surface 1532 of the outer container 1531 as shown in FIGS. 7A and 7B, for example, the outer container 1531 is not deformed due to a weight of the RFID tag 101, so that a measurement error can be reduced and the RFID tag 101 has the effect that its attached position is not limited.

In addition, the radio-type transmitting device with small-sized and lightweight can be used instead of a constitution for measuring liquid-level which has been used as a conventional method of managing the volume of a container and in which the conductivity or permittivity of the content, and the reflection of the ultrasonic wave are used can be substituted for. Thus, the radio-type transmitting device can realize to use a component in common, the component being able to memorize management information of the fuel cell system, for example, a fuel concentration, properties of a content, a recycling number of a fuel cartridge, or the like, and manage a volume. Therefore the radio-type transmitting device can achieve the superior effects of weight reduction with downsizing of a container. Components for managing the volume of the container which have been used before will not be necessary, if a whole size of the container is not changed. So, a space for storing the fuel can be bigger. Thus, it can be realized to drive the fuel cell system for a longer time.

The fuel cell unit 220 comprises a power generation cell 221 to which the methanol solution 1511 is directly supplied for generating electricity power, a fuel supply pump 222 which can be connected to the container 150 and supplies the methanol solution 1511 from the container 150 to the power generation cell 221, a voltage conversion circuit 223 for converting the power generated in the power generation cell 221 to a voltage appropriate for the electronic device 210 and supply the voltage to the electronic device 210, and the external transmitting/receiving apparatus 180 constituting the transmitting/receiving system 190. The external transmitting/receiving apparatus 180 transmits detected remaining amount information of the methanol solution 1511 to the controller 211 having a microcomputer and included in the electronic device 210.

Figure 10:
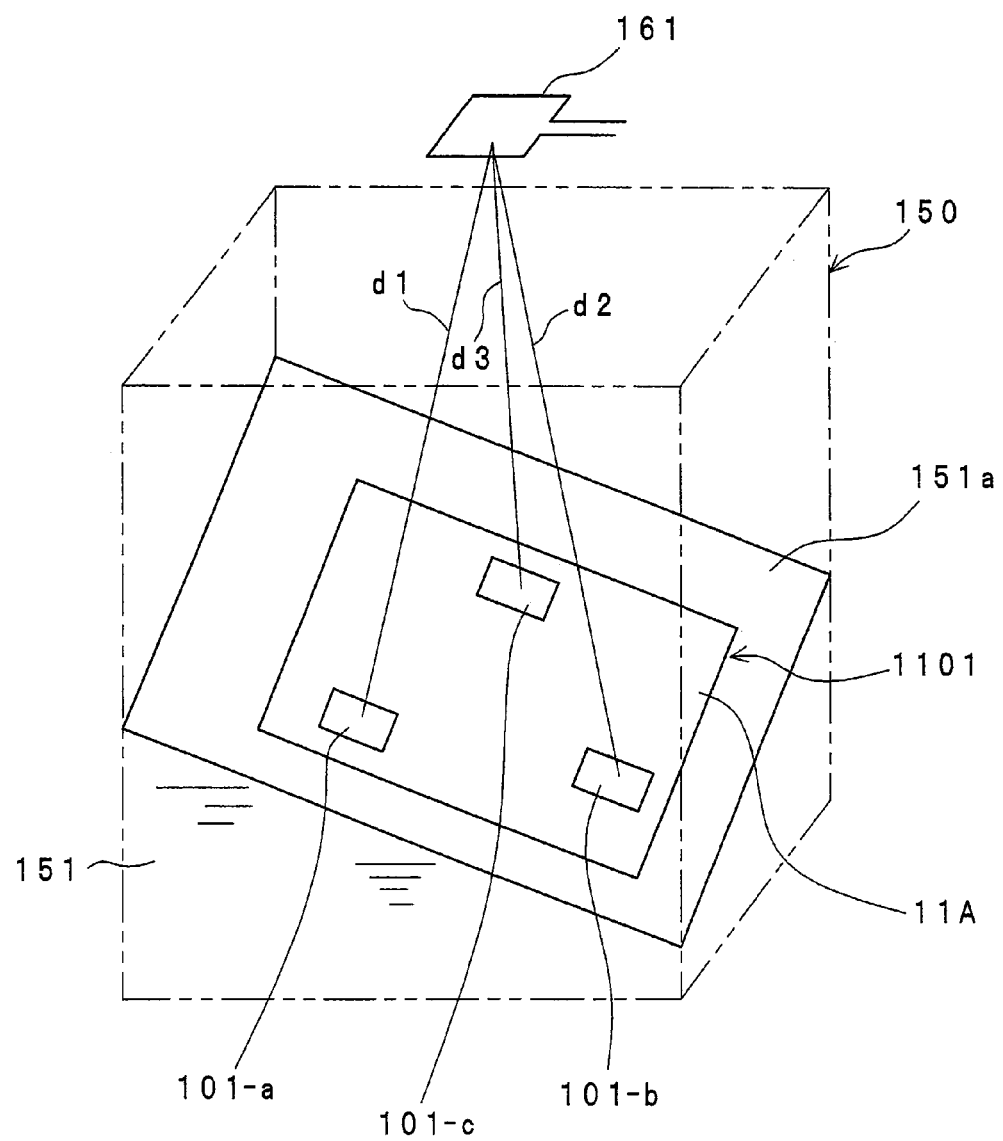
FIG. 10 is a view showing an example of a radio-type transmitting device which can be used in a case a liquid surface posture is inclined.

In addition, when the container 150 is mounted on the portable electronic device 210, a case where the distance 140 between the RFID tag 101 and the external transmitting/receiving apparatus 180 is not constant because the liquid surface 151a is moved in accordance with the changing of the posture of the container 150 may be considered. In order to solve such problem, a constitution shown in FIG. 10 is employed, for example. That is, a RFID tag 1101 is used on which three radio-type transmitting units 101-a, 101-b, and 101-c are arranged on one base member 11A in a state that positional relation thereof is fixed, each of the units 101-a, 101-b, and 101-c including the IC chip 120 and the antenna 12. The RFID tag 1101 is floated on the liquid surface 151a of the liquid 151 in the container 150. Meanwhile, a single antenna 161 is provided in the external transmitting/receiving apparatus 180. In addition, FIG. 10 illustrates a state that the liquid surface 151a is inclined with respect to the antenna 161 of the external transmitting/receiving apparatus 180. According to the above constitution, even when the liquid surface 151a is varied in accordance with the changing of the posture of the container 150, the distance 140 between the antenna 161 and the liquid surface 151a can be determined in spite of the posture of the liquid surface 151a by using distances d1, d2 and d3 between the antenna 161 and the three radio-type transmitting units 101-a, 101-b, and 101-c, respectively.

A description will be made of a fuel remaining amount management method in the application system 201 having the above constitution.

When a confirmation command for information regarding a fuel is generated from the controller 211 of the electronic device 210 to the external transmitting/receiving apparatus 180 of the fuel cell unit 220, the transmitting device controller 170 of the external transmitting/receiving apparatus 180 transmits a data return command to the RFID tag 101 at a constant power in order to read data stored in the RFID tag 101 in the container 150, that is, characteristic data of the fuel, for example. The RFID tag 101 which received the radio wave sends the data and the digitalized receiving voltage information 1291 which was digitalized by the encoding circuit 129 to the external transmitting/receiving apparatus 180 by control of the controller 126 of the RFID tag 101. Thus, the external transmitting/receiving apparatus 180 receives the data showing the fuel for the fuel cell and the receiving voltage information 1291 from the RFID tag 101.

The transmitting device controller 170 of the external transmitting/receiving apparatus 180 obtains the distance information 140 between the external transmitting/receiving apparatus 180 and the RFID tag 101 based on the receiving voltage information 1291 as described above. Thus, the remaining amount of the methanol solution 1511 in the container 150 can be detected.

After the characteristic data of the fuel such as a concentration of the methanol solution 1511 and the contents amount in the container 150 is confirmed, the methanol solution 1511 is drawn from the container 150 by the fuel supply pump 222 and supplied to the power generation cell 221, so that the power generation cell 221 starts generating the power. The power generated in the power generation cell 221 is converted to a predetermined voltage at the voltage conversion circuit 223 and supplied to the electric device 210.

After the power generation is started, the external transmitting/receiving apparatus 180 communicates with the RFID tag 101 periodically to receive the information of the receiving voltage information 1291 from the RFID tag 101, and manages the remaining amount of the methanol solution 1511 in the container 150 each time. When it is determined that the remaining amount of the methanol solution 1511 arrives at the predetermined value or less, the external transmitting/receiving apparatus 180 transmits that fact to the controller 211 of the electronic device 210. Thus, a message saying that the remaining amount of the fuel is low or the like is displayed on the electronic device 210 so as to urge exchanging or filling the fuel in the electric device, for example. Liquid-level information measured regularly can be stored into at least one of the external transmitting/receiving apparatus 180 and the RFID tag 101. Further, an expected remaining time for driving the fuel cell system can be displayed on the basis of the stored liquid-level information and the amount of time elapsed of measuring.

In addition, although the RFID tag 101 sends the receiving voltage information 1291 to the external transmitting/receiving apparatus 180 in the above fuel remaining amount management method in the application system 201, it may send the distance information 140 as described above. Further, the external transmitting/receiving apparatus 180 transmits the radio wave with a predetermined output voltage in a case when the apparatus 180 decides a distance between the antenna 161 of the apparatus 180 and the antenna 12 of the RFID tag 101, and the apparatus 180 can communicate with the RFID tag 101 with another output voltage in a case other than the decision of the distance.

Another example of the above-mentioned applied system having the transmitting/receiving system 190 and the like will be described below.

Figure 11:
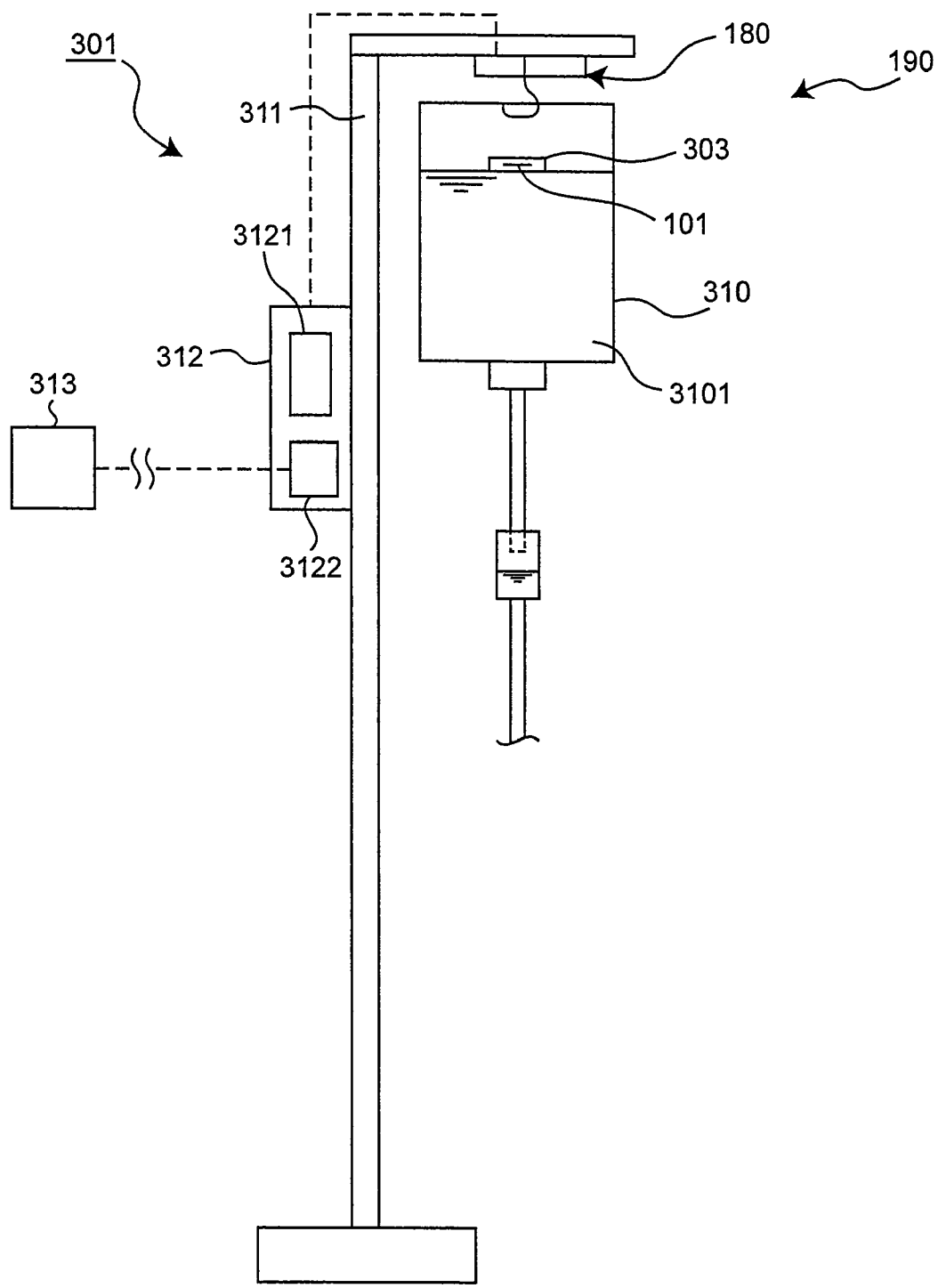
FIG. 11 is a view showing the other example of the system including the transmitting/receiving system according to the embodiment of the present invention.

FIG. 11 shows a configuration in which the transmitting/receiving system 190 having the external transmitting/receiving apparatus 180 and the RFID tag 101 is applied to an infusion management system 301. The infusion management system 301 is an example in which the transmitting/receiving system 190 is applied to an infusion container used for instillation in medical locations such as hospitals. Note that the medical infusion is used as an example in this embodiment, however, the transmitting/receiving system 190 can be applied to not only medical ones but also an infusion management system having the configuration in which liquid in a container is discharged.

The infusion management system 301 has an infusion container 310 such as an infusion bag, the external transmitting/receiving apparatus 180 and an infusion control unit 312. The infusion container 310, the external transmitting/receiving apparatus 180 and the infusion control unit 312 can be separately held in distinct supporting members. However, as shown in the figure, it is preferred that they are integrally held in an infusion holder 311 included in the infusion management system 301. Furthermore, the infusion management system 301 can include a display device 313 described later.

An infusion 3101 is stored in the infusion container 310 and a member 303 that embeds or mounts the RFID tag 101 as the radio-type transmitting device therein or thereon floats on a surface of the infusion 3101. A capsule that is formed of a material harmless to infusion and stores the RFID tag 101 therein may be used as an example of the member 303. Specifically, a same material as a material forming the infusion container 310 may be used. An information storage unit 127 in the RFID tag 101 stores information on the infusion 3101 of the infusion container 310, for example, management information 1271 including type, concentration, capacity, expiration date of a drug and information on the infusion container, as ID information. Information on a patient who intravenously receives the infusion 3101 may be included in the management information 1271.

In the infusion management system 301, the external transmitting/receiving apparatus 180 and the infusion control unit 312 are installed to the infusion holder 311. The infusion control unit 312 corresponds to a control part that controls the state of the infusion 3101 in the infusion container 310, is connected to the external transmitting/receiving apparatus 180 with or without wires and has a microcomputer 3121 and a communication device 3122. The microcomputer 3121 executes processing concerning management of the state of the infusion 3101 in the infusion container 310. The communication device 3122 sends information on infusion management to the display device 313 installed separately from the infusion container 310, the external transmitting/receiving apparatus 180 and the infusion control unit 312. The external transmitting/receiving apparatus 180 and the infusion control unit 312 may be integrally configured. In this configuration, the display device 313 may be attached to the infusion control unit 312 or the external transmitting/receiving apparatus 180.

As in the above-mentioned embodiments, in the infusion management system 301, the transmitting device controller 170 included in the external transmitting/receiving apparatus 180 obtains a communication distance between the external transmitting/receiving apparatus and the RFID tag 101 and then, obtains liquid level of the infusion 3101 on the basis of the communication distance. Here, the transmitting device storage unit 1711 included in the distance determination unit 171 provided with the transmitting device controller 170 has, in this example, a plurality of tables corresponding to a plurality of infusion containers 310. Using a table corresponding to the used infusion container 310, the distance determination unit 171 obtains the communication distance to the RFID tag 101. Furthermore, it is preferred that information on the patient is stored in the transmitting device storage unit 1711.

In this case, the transmitting device controller 170 also verifies the patient by communication with the RFID tag 101 in the infusion container 310.

Operations of the infusion management system 301 thus configured will be described.

When the infusion container 310 is attached at the infusion holder 311, the external transmitting/receiving apparatus 180 communicates with the RFID tag 101 and reads the ID information stored in the information storage unit 127 of the RFID tag 101. In a case that the information on the patient who intravenously receives the infusion 3101 is contained in the ID information, the transmitting device controller 170 compares the patient information with patient information previously recorded in the transmitting device controller 170. As a result of comparison, when determination is made that the infusion container 310 is suitable for the patient by coincidence of the patient information, instillation can be started. Through regular communication between the RFID tag 101 and the external transmitting/receiving apparatus 180, the liquid level of the infusion 3101 is measured. When the liquid level measured by the external transmitting/receiving apparatus 180 becomes predetermined level or lower, the transmitting device controller 170 outputs a residual quantity decrease signal to the infusion control unit 312.

On the other hand, as a result of the comparison of the patient information by the transmitting device controller 170, when the transmitting device controller 170 determines that the infusion container 310 is not suitable for the patient, the transmitting device controller 170 outputs an alarm signal to the infusion control unit 312. Similarly, when the transmitting device controller 170 determines the expiration of the infusion 3101, the transmitting device controller 170 outputs the alarm signal to the infusion control unit 312.

When receiving the residual quantity decrease signal or the alarm signal, the microcomputer 3121 included in the infusion control unit 312 instructs the communication device 3122 to send the signal and allows the display device 313 installed in a separate room such as a nurse station to display "low infusion residual quantity", "wrong infusion container" or the like to call upon replacement of the infusion or attention to the user of the infusion management system 301 such as a nurse and a doctor. Alternatively, on request of the user, the residual quantity of the infusion container 310 can be confirmed on real time.

According to the above-mentioned infusion management system 301, the following effects can be obtained.

That is, since the residual quantity of the infusion 3101 can be managed, the timings of infusion replacements to many patients can be informed individually. Thus, the nurse and the doctor are released from the burdensome operation associated with lack in the infusion.

Since the member 303 provided with the RFID tag 101 can be made in the size on the order of a few millimeters square, the system 301 can also be applied to a compact infusion container 310.

Further, since it is possible to verify whether or not the infusion is suitable for the patient, the system 301 has an excellent effect of preventing medical malpractice such as instillation of the wrong infusion.

Furthermore, although the infusion container used for instillation is used on the above-mentioned example, this embodiment can also be applied to a blood transfusion pack used for blood transfusion and the residual quantity and blood type of blood for transfusion can be managed.

The embodiments described with reference to FIG. 7, FIG. 8 and FIG. 10 can also be applied to the infusion management system 301.

Although the RFID tag 101 is used as an example of the radio-type transmitting device, the example is not limited to the RFID tag 101.

Although the transmitting device controller 170 of the external transmitting/receiving apparatus 180 measures the communication distance using a table corresponding to the used infusion container, the communication distance may be obtained according to a predetermined calculation corresponding to the infusion container solution.

Communication of the signals such as the residual quantity decrease signal from the infusion control unit 312 to the display device 313 may be performed with wires. When communication is performed without wires, frequencies that do not interfere communication between the external transmitting/receiving apparatus 180 and RFID tag 101 may be adopted.

A power source for the infusion control unit 312 may be acquired from commercial power or by cordless means using a rechargeable battery.

Figure 12A:
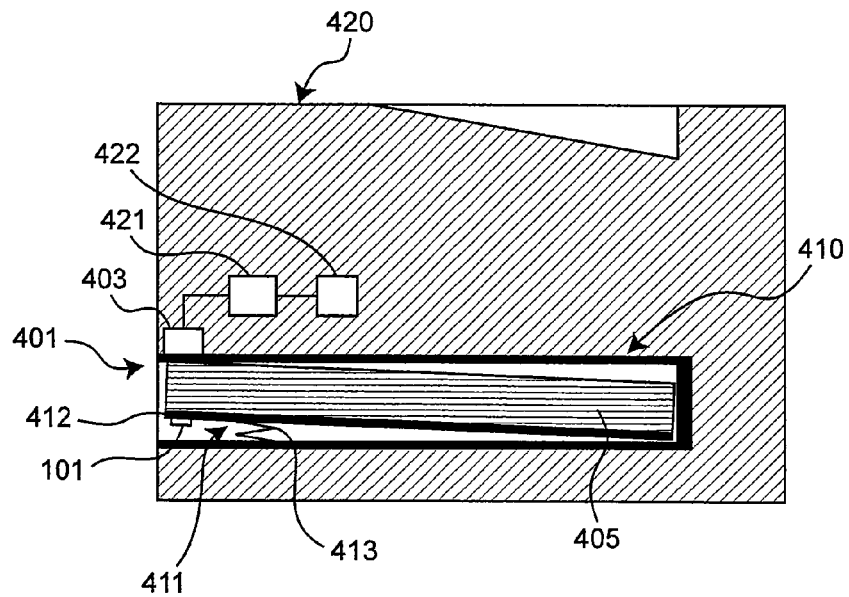
FIG. 12A is a view showing another example of the system including the transmitting/receiving system according to the embodiment of the present invention.
Figure 12B:
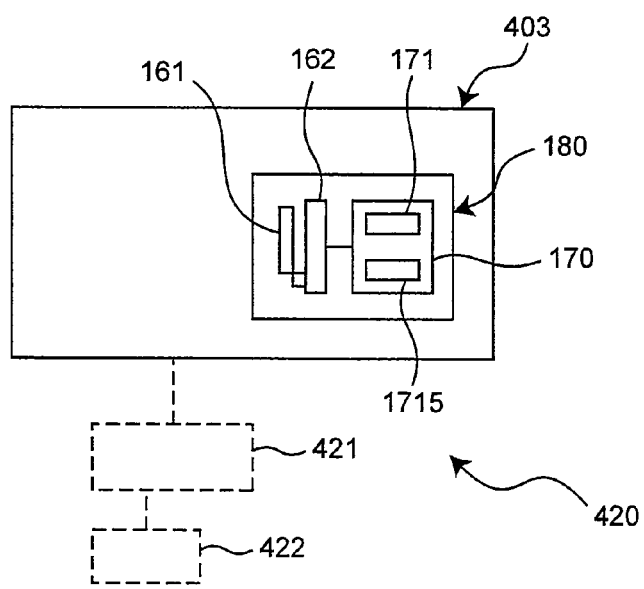
FIG. 12B is a block diagram explaining a constitution of a measurement unit shown in FIG. 12.

Next, FIG. 12A and FIG. 12B show configurations in which the transmitting/receiving system 190 equipped with the external transmitting/receiving apparatus 180 and the RFID tag 101 is applied to a printer paper residual quantity management device 401. The printer paper residual quantity management device 401 is an example in which the transmitting/receiving system 190 is applied to a paper feeding part of a printer 420.

The printer paper residual quantity management device 401 has a sheet tray 410 corresponding to an example of a container for storing printing papers 405 as content, capacity of which varies, therein, a paper feeding mechanism 411 with the RFID tag 101 provided in the sheet tray 410 and a measurement unit 403 having the external transmitting/receiving apparatus 180. The paper feeding mechanism 411 has a mounting member 412 that mounts the printing papers 405 thereon and attaches the RFID tag 101 thereto and an urging member 413 that allows the mounting member 412 to be movable within the sheet tray 411 depending on change in the quantity of the printing paper 405 and allows the sheet tray 411 to feed the printing papers 405 to the printer 420 irrespective of the residual quantity of the printing papers 405.

In this example, a spring is used as an example of the urging member 413 and the paper feeding mechanism 411 presses the printing papers 405 mounted on the mounting member 412 on a side of the main body of the printer 420 with a force of the urging member 413.

In this example, the information storage unit 127 of the RFID tag 101 equipped with the mounting member 412 stores the management information 1271, for example, ID information and information on the printing papers 405 stored in the sheet tray 410 including size, type, etc. therein. The RFID tag 101 is attached to, for example, a central part of the mounting member 412 in the width direction thereof.

The measurement unit 403 is installed at the location corresponding to the RFID tag 101 on the side of the printer 420 to which the sheet tray 410 can be loaded. As in the above-mentioned embodiments, the transmitting device controller 170 of the external transmitting/receiving apparatus 180 included in the measurement unit 403 obtains the communication distance to the RFID tag 101 and then, obtains the residual quantity of the printing papers 405 on the basis of the obtained communication distance. The transmitting device controller 170 is provided with a residual quantity determination unit 1715 that stores information on relationship between the communication distance and the residual quantity of the printing papers 405 and reads the information on relationship. The measurement unit 403 is further connected to a printer control unit 421 provided in the printer 420.

Operations of the printer paper residual quantity management device 401 thus configured will be described below.

After the sheet tray 410 is loaded into the printer 420, the external transmitting/receiving apparatus 180 provided in the measurement unit 403 measures the residual quantity of the printing paper 405 on a regular basis. When the measured paper residual quantity becomes predetermined quantity or less, the transmitting device controller 170 outputs a residual quantity decrease signal to the printer control unit 421. On receipt of the residual quantity decrease signal, the printer control unit 421 allows, for example, a display unit 422 of the printer 420 or a display screen 422 of a personal computer that is connected to the printer 420 and issues a printing command to display "low paper residual quantity" or the like to urge the user of the printer 420 to fill the printing papers 405. Furthermore, on request of the user, the residual quantity and size of paper in the sheet tray 410 can be confirmed on real time.

According to the above-mentioned printer paper residual quantity management device 401, the following effects can be obtained.

By communication between the external transmitting/receiving apparatus 180 and the RFID tag 101, the residual quantity of the printing papers 405 can be managed.

Further, since the RFID tag 101 can be made in the size on the order of a few millimeters square, the RFID tag 101 can be mounted in any space in the printer.

Furthermore, by referring to information contained in a reply signal sent from the RFID tag 101 to the measurement unit 403, for example, information on the type and size of the printing papers 405, when the printing command is issued from the personal computer connected to the printer 420, the different printing papers 405 in size can be prevented from being designated.

Although the RFID tag is described as an example of the radio-type transmitting device, the radio-type transmitting device is not limited to the RFID tag.

Figure 13A:
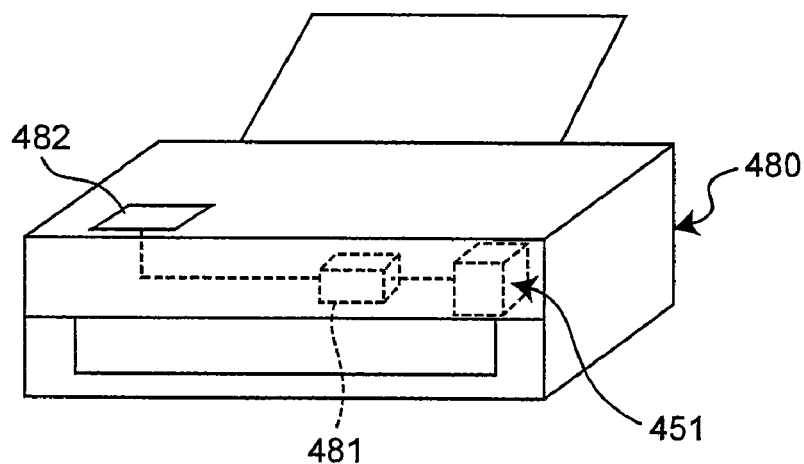
FIG. 13A is a view showing a further example of the system including the transmitting/receiving system according to the embodiment of the present invention.
Figure 13B:
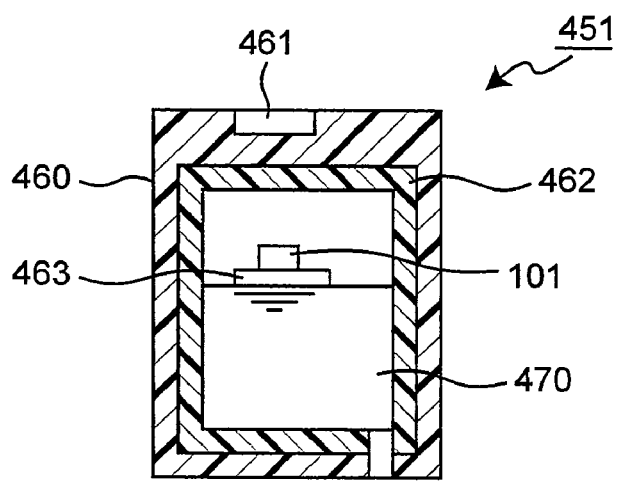
FIG. 13B is a block diagram showing a constitution of an ink residual quantity management apparatus shown in FIG. 13A.
Figure 13C:
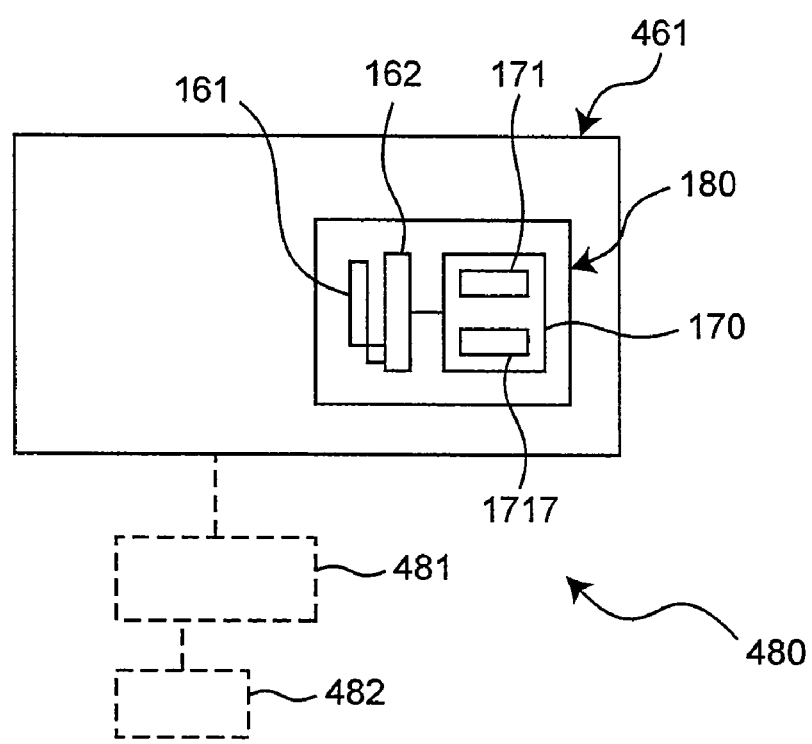
FIG. 13C is a block diagram explaining a constitution of a measurement unit shown in FIG. 13B.

Next, FIG. 13A to FIG. 13C show configurations in which the transmitting/receiving system 190 equipped with the external transmitting/receiving apparatus 180 and the RFID tag 101 are applied to a printer ink residual quantity management apparatus 451. The ink residual quantity management apparatus 451 in this example has the configuration in which the transmitting/receiving system 190 is applied to an ink cartridge for an ink jet printer.

The ink residual quantity management apparatus 451 includes a measurement unit 461 with the external transmitting/receiving apparatus 180; an ink cartridge 462 which corresponds to an example of a container for storing ink 470 as content, capacity of which varies, therein, and has the RFID tag 101; and an ink holder 460 that accommodates the ink cartridge 462 therein and is equipped with the measurement unit 461.

The ink holder 460 exchangeably accommodates the ink cartridge 462 therein. A member 463 equipped with the RFID tag 101 floats on the ink 470 stored in the ink cartridge 462. The information storage unit 127 of the RFID tag 101 stores as the management information 1271, in this example, ID information and information on the ink 470 stored in the ink cartridge 462 such as color and type, etc.

The measurement unit 461 executes processing concerning management of the residual quantity of the ink 470 in the ink cartridge 462. As in the above-mentioned embodiments, the transmitting device controller 170 of the external transmitting/receiving apparatus 180 included in the measurement unit 461 obtains the communication distance to the RFID tag 101 and then, obtains the residual quantity of the ink 470 on the basis of the obtained communication distance. As shown in FIG. 13C, the transmitting device controller 170 is provided with a residual quantity determination unit 1717 that stores information on relationship between the communication distance and the residual quantity of the ink 470 and reads the information on relationship. The measurement unit 461 is connected to a printer control unit 481 provided in the printer 480.

Operations of the ink residual quantity management apparatus 451 thus configured will be described below.

In the state where the ink cartridge 462 is attached to the ink holder 460, the external transmitting/receiving apparatus 180 of the measurement unit 461 measures the residual quantity of the ink 470 on a regular basis. When the measured ink residual quantity becomes predetermined quantity or less, the transmitting device controller 170 of the external transmitting/receiving apparatus 180 outputs a residual quantity decrease signal to the printer control unit 481.

On receipt of the residual quantity decrease signal sent from the transmitting device controller 170, the printer control unit 481 allows, for example, a display unit 482 of the printer 480 or a display screen 482 of a personal computer that is connected to the printer 480 and issues a printing command to display "low ink residual quantity" or the like to urge the user of the printer 480 to replace the ink cartridge 462. Furthermore, on request of the user, the residual quantity of ink in the ink cartridge 462 can be confirmed on real time.

According to the above-mentioned ink residual quantity management apparatus 451, the following effects can be obtained.

By communication between the external transmitting/receiving apparatus 180 and the RFID tag 101, the residual quantity of the ink 470 in the ink cartridge 462 can be managed.

Further, since the RFID tag 101 can be made in the size on the order of a few millimeters square, the RFID tag 101 can be mounted in a compact ink cartridge.

Although the RFID tag is described as an example of the radio-type transmitting device, the radio-type transmitting device is not limited to the RFID tag.

Furthermore, the ink cartridge 462 having the RFID tag 101 may adopt the configurations described with reference to FIG. 7A, FIG. 7B and FIG. 8.

Second Embodiment

As described above, paying attention to the receiving sensitivity, the RFID tag 101 has adopt the configuration shown in FIG. 1, that is, the configuration with the coding circuit 129. However, the configuration of the RFID tag is not limited to this and even a configuration with a function of detecting a communication error can obtain the same effects as the above-mentioned RFID tag 101. The communication error detection function will briefly described below.

That is, generally, in data communication assuming an error during communication, an error correction code such as Reed-Solomon code is added to data, and the data is modulated to an approved frequency band and transmitted. The received data is decoded after demodulation and a data portion having a transmission error is corrected using the error correction code to be correct data.

There are various methods of encoding communication data. The method in which it is easy to determine 1 or 0 in its communication path when data is decoded is selected. 1 or 0 is determined according to relative comparison of 1 to 0 at a constant threshold level.

In encoding and decoding of the signal level of communication data, when there is no nonlinear component in the communication path, the received communication data is completely decoded and erroneous data processing never occurs. On the contrary, when noise occurs in the communication path, assuming that the noise components generate in certain probability distribution, the erroneous data processing is done at a certain probability with a relative relationship between data and noise.

As to whether or not data is wrongly determined, by adding the error correction code to data to be sent, transmitting/receiving the data and examining the relationship between the decoded data and the error correction code, an error point, that is, communication error point can be determined. However, when errors beyond the correction capability occur in the decoded data, the errors can be recognized but cannot be corrected.

Figure 16A:
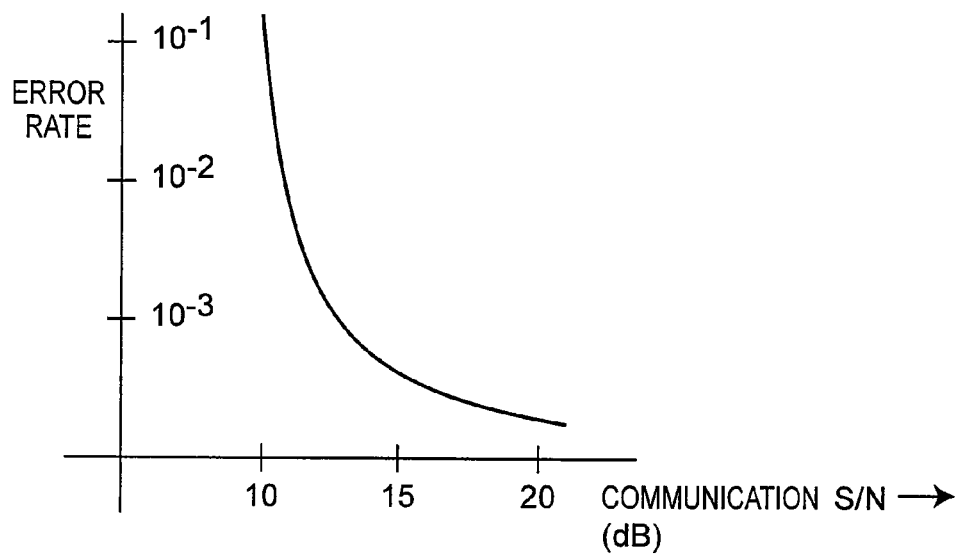
FIG. 16A is a graph showing a relation between communication S/N and rate of error.

The probability of occurrence of the communication error depends on the distribution of noise. Assuming that the noise distribution is Gauss distribution, this results in a graph as shown in FIG. 16A.

In the case of the RFID tag, the receive signal is decreased by the square of the distance of the communication path. Thus, assuming that noise in the communication path is constant, S/N deteriorates by the square of the distance of the communication path. When an error occurs during communication, as described above, the error point can be identified from the relationship between the added error correction code and data and the number of errors, that is, the number of error points can be also detected. When the communication distance exceeds a predetermined distance and errors more than assumed occur, the excessive errors can be recognized but the error points cannot be identified. On the other hand, as shown in FIG. 16B, as long as the communication distance falls within an error detectable range (KL), the communication distance can be accurately measured on the basis of the number of errors.

Figure 16B:
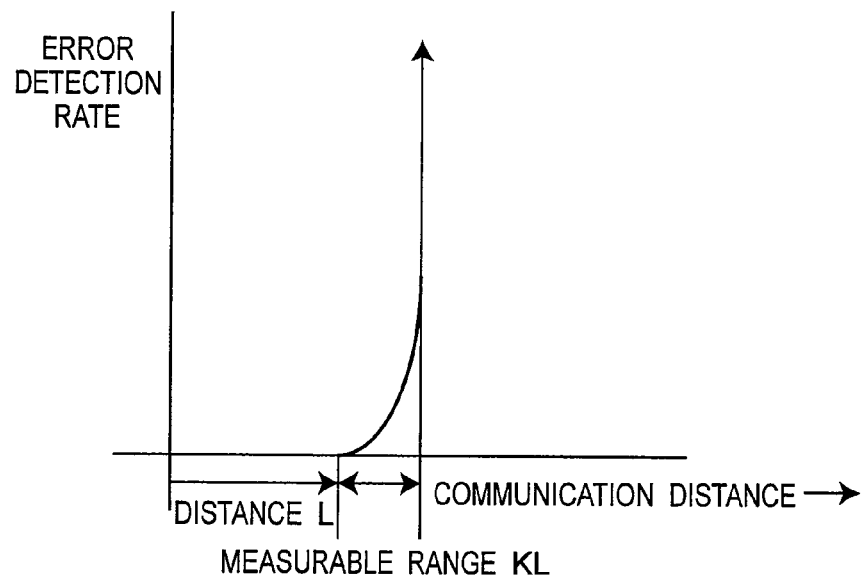
FIG. 16B is a graph showing a relation between communication distance and number of detected error.

As shown by "distance L" in FIG. 16B, the communication distance, that is, the distance between the RFID tag and the external transmitting/receiving apparatus is too short, the receiving intensity becomes too high. In this case, since no error occurs, there is a possibility that the communication distance cannot be measured.

Figure 14:
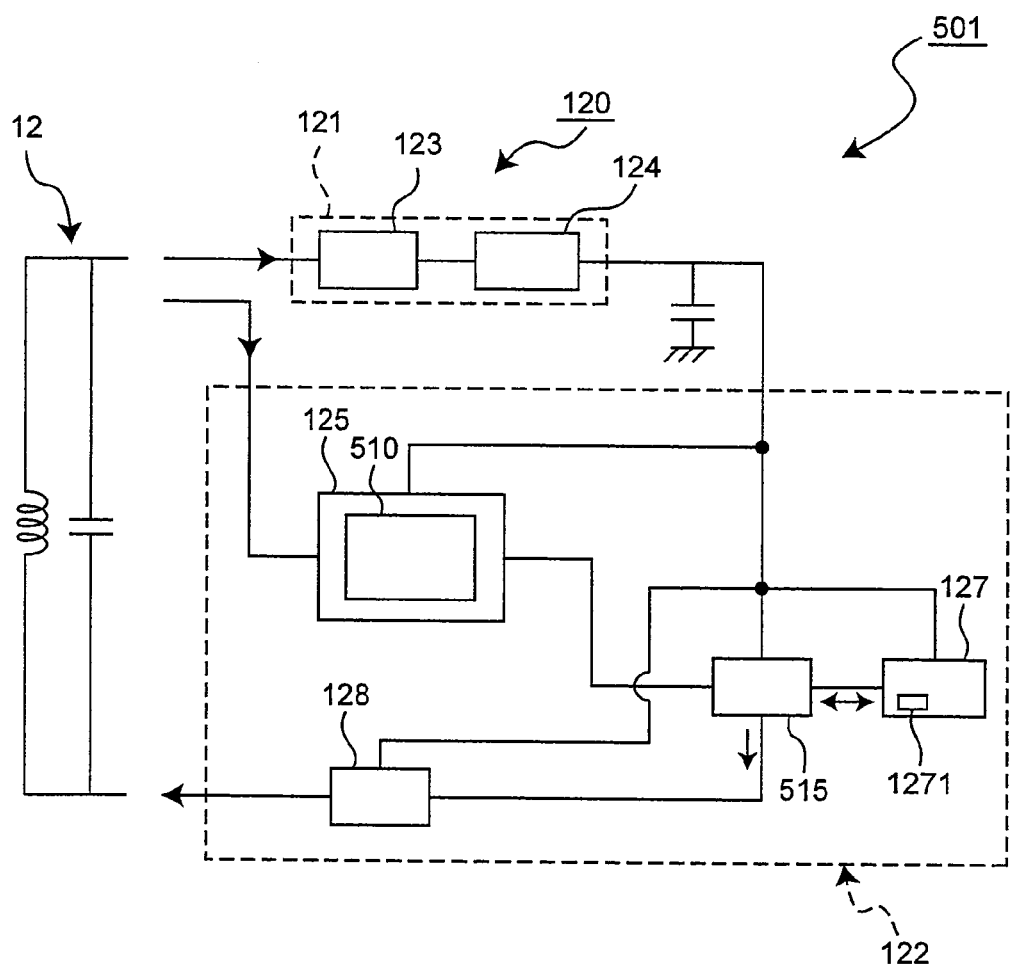
FIG. 14 is a block diagram showing a constitution of another radio-type transmitting device according to an embodiment of the present invention.

In the second embodiment, paying attention to the above-mentioned relationship between the communication distance and the number of errors, the communication distance is obtained on the basis of the number of errors contained in the concept of communication error. In other words, the RFID tag may employ a configuration with a function of detecting the communication error. FIG. 14 shows an example of the configuration.

An RFID tag 501, shown as an example of the radio-type transmitting device in FIG. 14, has a communication error detecting circuit 510 in place of the encoding circuit 129 in the RFID tag 101 and a controller 515 in place of the controller 126. The communication error detecting circuit 510 is contained in the receive circuit 125 as a concept. The receive circuit 125 is connected to the controller 515. The other configuration is the same as the configuration of the RFID tag 101 shown in FIG. 1.

The communication error detecting circuit 510 is a circuit for detecting the communication error of a radio wave transmitted from the external transmitting/receiving apparatus. Specifically, the communication error detecting circuit 510 receives power from the power supply voltage generating unit 121, detects the number of errors of the radio wave received by an antenna 12 as an example of error information corresponding to the communication error, and sends the detected number of errors to the controller 515.

Similarly to the controller 126, the controller 515 serves to control the RFID tag 501 and executes a predetermined command supplied from the receive circuit 125. In the case of data writing, the controller 515 writes the result to the information storage unit 127 and in the case of data reading, reads data from the information storage unit 127 and sends back the data from the loop antenna 12 via the send circuit 128. On the other hand, in the RFID tag 501 in this embodiment, the controller 515 performs control so as to modulate the error information supplied from the communication error detecting circuit 510 to radio frequency band in the send circuit 128, supply power to the loop antenna 12 as radio wave and send it to the external transmitting/receiving apparatus 180. Alternatively, the controller 515 performs control so as to obtain the communication distance to the external transmitting/receiving apparatus 180 on the basis of the error information, modulate the distance information to radio frequency band in the send circuit 128, supply power to the loop antenna 12 as radio wave and send it to the external transmitting/receiving apparatus 180.

Similarly to the controller 126, the controller 515 has a conversion unit 1261 and a storage unit 1262. The storage unit 1262 provided in the controller 515 stores information on relationship between the number of selected levels described later and the communication distance and relationship between the number of errors and the communication distance therein.

Figure 15:
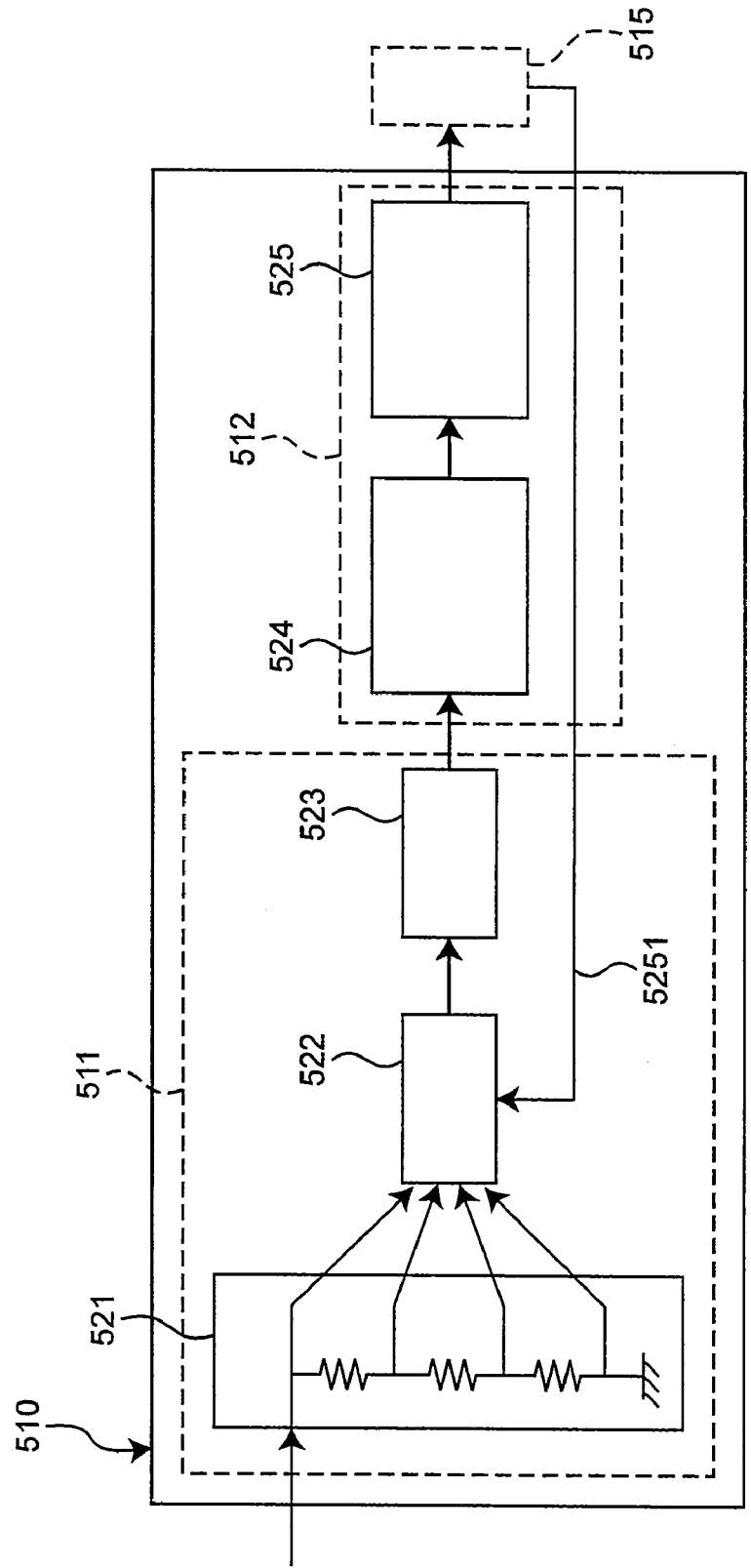
FIG. 15 is a block diagram showing a constitution of a communication error detecting circuit shown in FIG. 14.

As described above, in the range represented by "distance L" in FIG. 16B, in which the distance between the RFID tag and the external transmitting/receiving apparatus is too short, the communication distance cannot be conventionally measured. To solve this problem, in the RFID tag 501 in this embodiment, the communication error detecting circuit 510 employs a configuration shown in FIG. 15.

That is, with respect to function, the communication error detecting circuit 510 has a signal intensity changing unit 511 and an error determination unit 512. The signal intensity changing unit 511 serves to change an intensity of the radio wave received by the antenna 12 and has a level change circuit 521, a selection circuit 522 and an amplification circuit 523. The level change circuit 521 is formed of, for example, a resistive dividing circuit having a plurality of resistances and forcibly changes the signal intensity of the radio wave received by the antenna 12 by selecting a combination of the plurality of resistances. The selection circuit 522 is connected to the level change circuit 521, and among a plurality of received radio waves each having distinct signal intensity supplied from the level change circuit 521, selects the received radio wave having optimum signal intensity according to a selection signal 5251 sent from the controller 515. The amplification circuit 523 is connected to the selection circuit 522 and amplifies the radio wave supplied from the selection circuit 522 with an amplification factor that makes a maximum distance to be measured measurable. Here, the maximum distance to be measured refers to a distance obtained by adding the distance L to the measurable range KL shown in FIG. 16B.

The error determination unit 512 is connected to the signal intensity changing unit 511, detects the communication error from the received radio wave, the intensity of which is changed, sends the detection result to the controller 515 and has a decoding circuit 524 and an error determination circuit 525. The decoding circuit 524 is connected to the amplification circuit 523, decodes the received radio wave supplied from the amplification circuit 523, detects a header of the decoded data and converts the data into an error detectable received data array. The error determination circuit 525 is connected to the decoding circuit 524, detects the number of errors from the received data array supplied from the decoding circuit 524 and sends the detected number of errors to the controller 515.

When the number of errors is not provided from the error determination circuit 525, the controller 515 sends the selection signal 5251 to the selection circuit 522 so that the selection circuit 522 may select the received radio wave having a signal intensity lower than the formerly output signal intensity.

The communication error detecting circuit 510 repeats change in signal intensity until the number of errors can be detected. When the communication error is detected, the communication error detecting circuit 510 sends an attenuation factor determined based on the combination of the resistances of the level change circuit 521, that is, the number of selected levels and the number of errors to the controller 515. The attenuation factor represents how much the signal intensity level of the radio wave received by the antenna 12 is lowered and is expressed as a ratio of used resistances to all resistances of the level change circuit 521.

Operations of the RFID tag 501 thus configured will be described below. Since the operation concerning communication with the external transmitting/receiving apparatus 180 is the same as that in the above-mentioned RFID tag 101, hereinafter, operation concerning the communication error detecting circuit 510 will be mainly described.

When the RFID tag 501 exists in the above-mentioned measurable range KL shown in FIG. 16B with respect to the external transmitting/receiving apparatus 180, in other words, the number of errors can be obtained the first time without repeating the above-mentioned change in signal intensity, the radio wave having the received signal intensity is used and the communication error detecting circuit 510 decodes the radio wave and detects the communication error, thereby detecting the number of errors. Based on the number of errors and the number of selected levels that are provided from the communication error detecting circuit 510 as an example of the error information, the controller 515 obtains communication distance information in the conversion unit 1261. The conversion unit 1261 obtains the distance L shown in FIG. 16B from the number of selected levels and a position in the measurable range KL shown in FIG. 16B from the number of errors. The controller 515 transmits the communication distance information to the external transmitting/receiving apparatus 180 via the send circuit 128 and the antenna 12. Furthermore, the controller 515 may transmit at least the number of errors to the external transmitting/receiving apparatus 180 without the conversion into communication distance information.

On the other hand, when the RFID tag 501 exists in the range of the distance L shown in FIG. 16B with respect to the external transmitting/receiving apparatus 180, as described above, the communication error detecting circuit 510 repeats change in signal intensity until the number of errors can be detected. That is, an input is attenuated by changing connection of the resistances of the level change circuit 521 and the signal level is selected until an error occurs. Then, since the number of errors is detected, the controller 515 obtains the communication distance information in the conversion unit 1261 on the basis of the number of errors and the number of selected levels that are provided from the communication error detecting circuit 510. The controller 515 controls to transmit the communication distance information to the external transmitting/receiving apparatus 180 via the send circuit 128 and the antenna 12. Alternatively, the controller 515 may control to transmit the number of errors and the number of selected levels of the selection circuit 522 to the external transmitting/receiving apparatus 180 without the conversion into the communication distance information. In this case, the number of errors and the number of selected levels correspond to error information.

As described above, even when the communication error detecting circuit 510 is provided to detect the communication error, similar effects to those in the case where communication distance information is obtained based on the receiving sensitivity can be obtained.

In each of the above-mentioned embodiments and examples of the applied system, the RFID tags 101, 501 adopt a mode of replying by use of power obtained by receiving the radio wave from the external transmitting/receiving apparatus 180. However, the reply mode from the RFID tags 101, 501 to the external transmitting/receiving apparatus 180 is not limited to the above-mentioned mode. For example, a so-called load modulation method of transmitting the reply signal of the radio-type transmitting device to the external transmitting/receiving apparatus 180 by modulating a receiving impedance of the antenna 12 at the time when the radio-type transmitting device receives radio wave may be employed. Also in this case, it is apparent that effects similar to those in the above-mentioned embodiments and examples of the applied system can be obtained.

That is, in the case of the radio-type transmitting device employing the load modulation method, there is no need to amplify the reply signal and reply from the antenna of the radio-type transmitting device. By changing the load impedance connected to the antenna with relative power saving according to the reply signal, the radio-type transmitting device employing the load modulation method makes a transmission load of the external transmitting/receiving apparatus 180 change, thereby enabling communication. The transmission power in the external transmitting/receiving apparatus 180 to the radio-type transmitting device at this time is a function of distance as described above. Since the reply signal level transmitted to the external transmitting/receiving apparatus 180 from the radio-type transmitting device according to the load modulation method is a function of distance as in transmission in the external transmitting/receiving apparatus 180, the same effects can be obtained.

Figure 17:
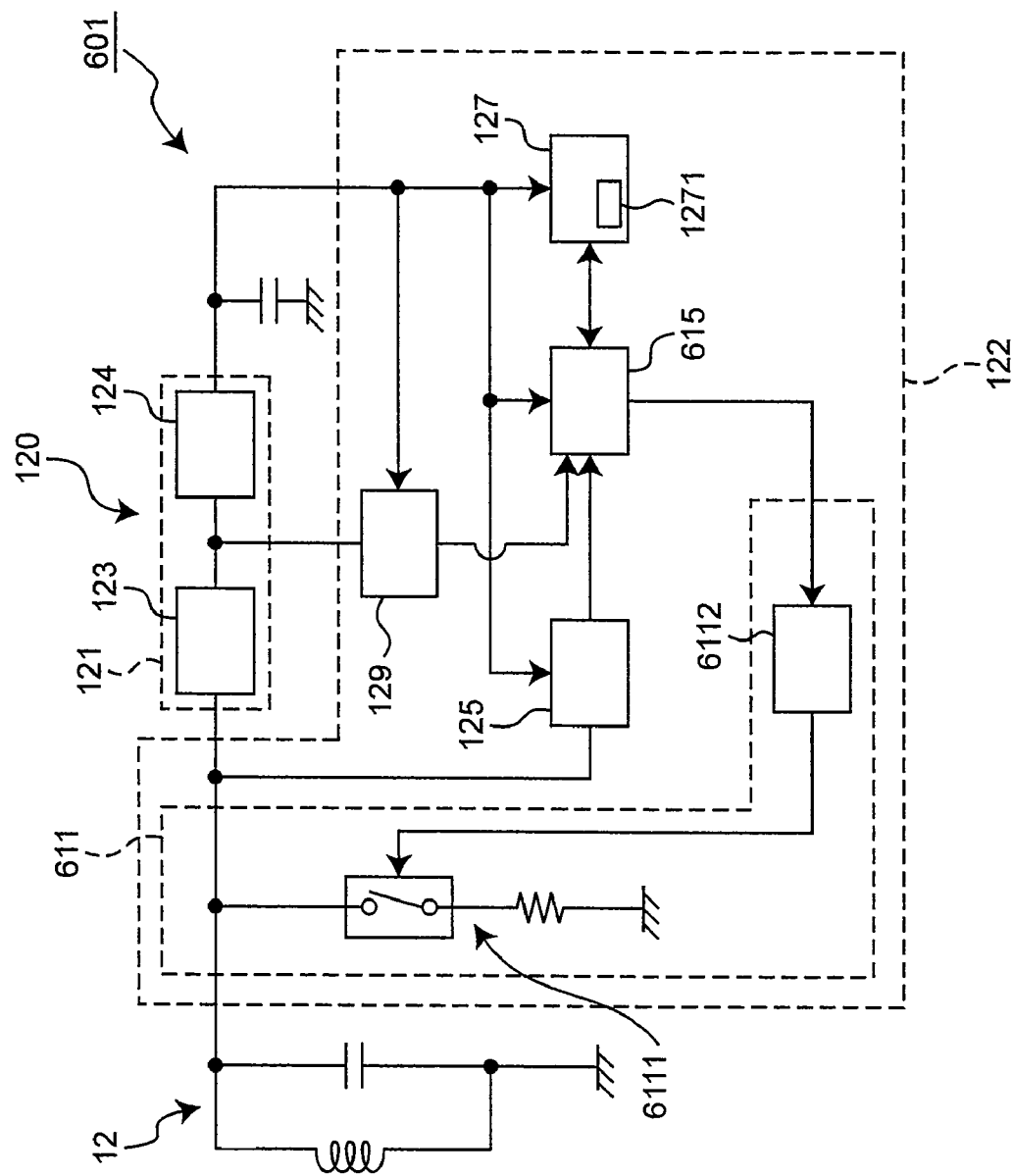
FIG. 17 is a block diagram showing a constitution of another radio-type transmitting device according to an embodiment of the present invention.

An RFID tag as an example of such radio-type transmitting device employing the load modulation method may adopt a configuration shown in FIG. 17.

That is, an RFID tag 601 shown in FIG. 17 performs load modulation on the basis of the receiving sensitivity in the RFID tag 601. As compared to the RFID tag 101 shown in FIG. 1, since there is no need to amplify and reply the reply signal as described above, the send circuit 128 becomes unnecessary. Thus, the RFID tag 601 adopts the configuration in which a load modulation unit 611 is provided in place of the send circuit 128 and a controller 615 is provided in place of the controller 126. The load modulation unit 611 has, for example, a switching unit 6111 which changes the load of the antenna 12 to modulate a receiving impedance of the antenna 12 and a load switching unit 6112 for switching the switching unit 611. The switching unit 6111 only needs to modulate the receiving impedance of the antenna 12, so the configuration thereof is not limited to the switch configuration shown in the figure.

The controller 615 controls the operation of the load switching unit 6112 on the basis of the receiving sensitivity encoded by the encoding circuit 129, specifically, on the basis of, for example, the communication distance information obtained from the receiving sensitivity.

An example of operations in the transmitting/receiving system equipped with the RFID tag 601 thus configured and the external transmitting/receiving apparatus 180 will be described.

As described in the first embodiment, in the RFID tag 601 that receives the radio wave transmitted from the external transmitting/receiving apparatus 180, the receiving sensitivity is encoded in the encoding circuit 129 and the encoded receiving sensitivity is supplied to the controller 615. Based on the encoded receiving sensitivity, the controller 615 controls operation of the load switching unit 6112 and thus the switching unit 6111 modulates the receiving impedance of the antenna 12 according to the communication distance information, for example. Through the modulation, the transmission load of the external transmitting/receiving apparatus 180 changes. Depending on the change, the external transmitting/receiving apparatus 180 can obtain the communication distance to the RFID tag 601.

Figure 18:
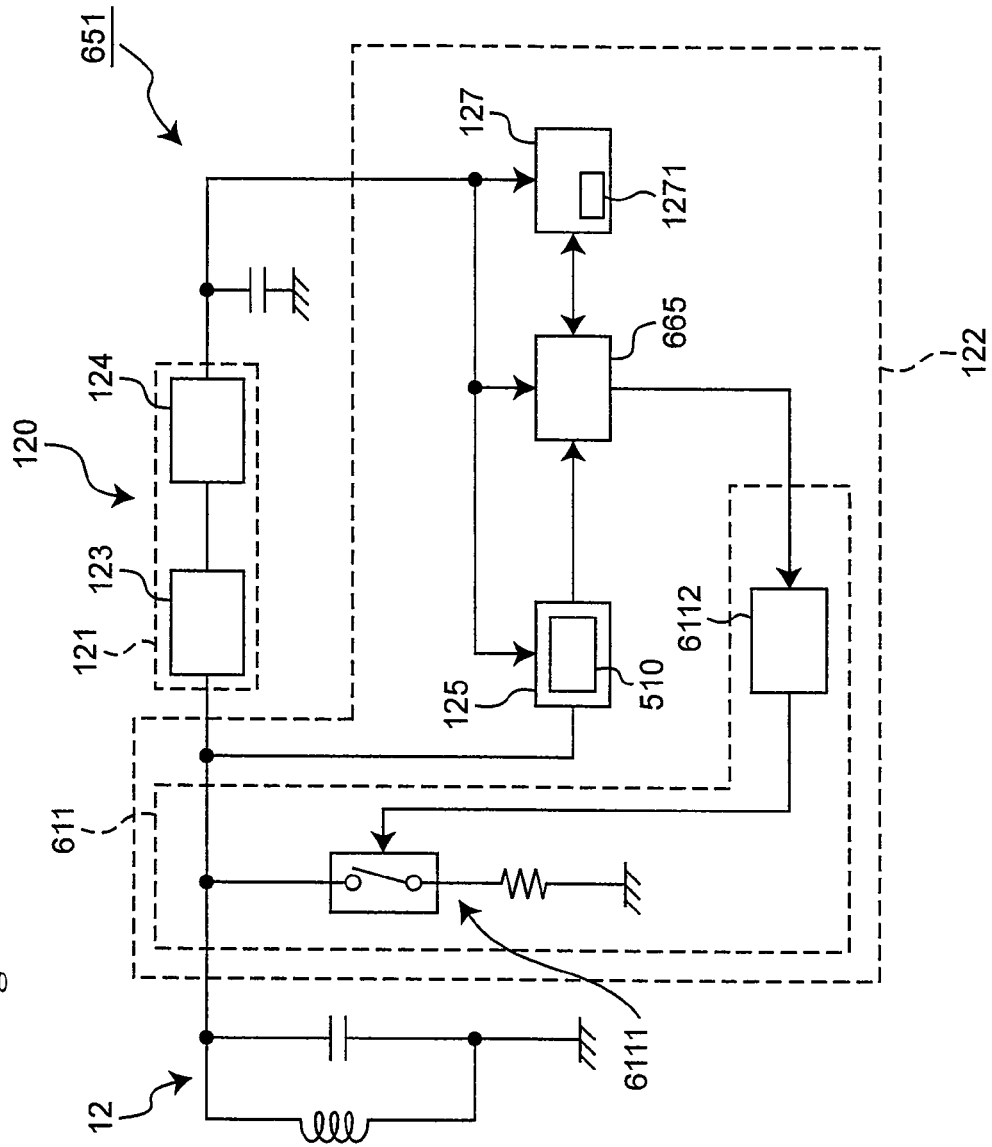
FIG. 18 is a block diagram showing a constitution of another radio-type transmitting device according to an embodiment of the present invention.
Figure 19:
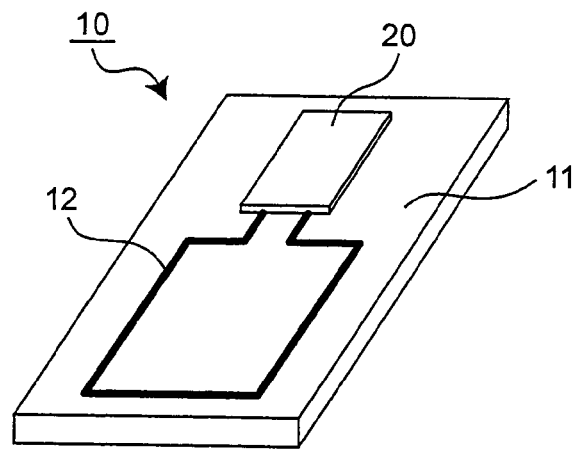
FIG. 19 is a perspective view showing a conventional RFID tag.
Figure 20:
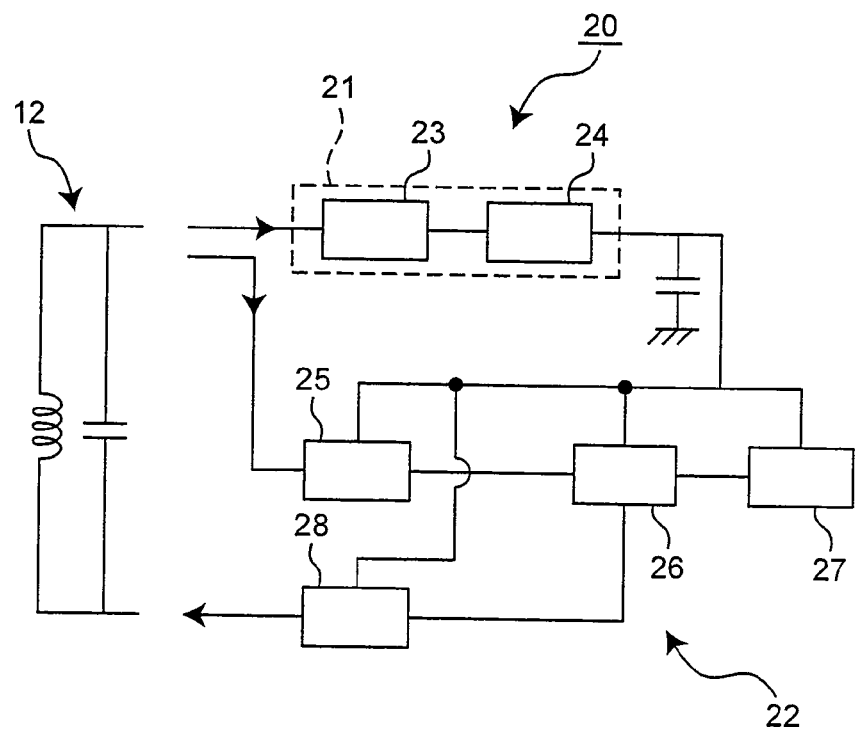
FIG. 20 is a block diagram showing a constitution of an IC chip of the conventional RFID tag.

Further, FIG. 18 shows a configuration example of a RFID tag that performs load modulation on the basis of the communication error described with reference to FIG. 14. In a RFID tag 651 shown in FIG. 18, based on the number of errors, a controller 665 controls operation of the load switching unit 6112 and thus the switching unit 6111 modulates the receiving impedance of the antenna 12. Through the modulation, the transmission load of the external transmitting/receiving apparatus 180 changes. Depending on the change, the external transmitting/receiving apparatus 180 can obtain the communication distance to the RFID tag 651.

As mentioned above, the present invention can be applied to a radio-type transmitting device which exchanges information with the external transmitting/receiving apparatus without any contact by a radio wave of a radio frequency band to manage an amount of contents in the container, for example; a container including the above radio-type transmitting device; a transmitting/receiving system including the above radio-type transmitting device; and a transmitting/receiving method.

The entire disclosures of Japanese Patent Applications No. 2005-195122 filed on Jul. 4, 2005 and No. 2006-162553 filed on Jun. 12, 2006 including specifications, claims, drawings, and summaries are incorporated herein by reference in its entirety.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A radio-type transmitting device comprising:
   a power supply voltage generating unit configured to receive a radio wave sent from an external transmitting/receiving apparatus and generate an internal power supply voltage;
   a transmission unit configured to transmit information to the external transmitting/receiving apparatus;
   a communication error detecting circuit configured to detect communication error in a received radio wave; and
   a controller configured to transmit error information corresponding to the communication error detected by the communication error detecting circuit from the transmission unit to the external transmitting/receiving apparatus.

2. The radio-type transmitting device according to claim 1, wherein the communication error detecting circuit includes a signal intensity changing unit configured to change intensity of the received radio wave and output a received radio wave with changed intensity; and an error determination unit connected to the signal intensity changing unit and configured to detect the communication error in the received radio wave with changed intensity and output a detected communication error to the controller, and the controller is configured to make the intensity of the received radio wave change in the signal intensity changing unit in accordance with the detected communication error.

3. The radio-type transmitting device according to claim 2, wherein in a case that the external transmitting/receiving apparatus transmits the radio wave having an error correction code, the communication error is an error count detected in error correction, the controller makes the intensity of the received radio wave change in the signal intensity changing unit in accordance with the error count.

4. The radio-type transmitting device according to claim 1, wherein the transmission unit is an antenna and is connected to the controller and the antenna; and has a load modulation unit configured to modulate an impedance of the antenna in accordance with the error information by control of the controller.

5. A transmitting/receiving method comprising:
receiving a radio wave transmitted from an external transmitting/receiving apparatus at a radio-type transmitting device to generate an internal power supply voltage;
transmitting information from the radio-type transmitting device to the external transmitting/receiving apparatus;
after generating the internal power supply voltage before transmitting information, detecting communication error in the radio wave transmitted from the external transmitting/receiving apparatus by the radio-type transmitting device; and
transmitting error information corresponding to a detected communication error from the radio-type transmitting device to the external transmitting/receiving apparatus.

6. The transmitting/receiving method according to claim 5, wherein, when it is difficult to detect the communication error, the radio-type transmitting device changes intensity of receiving signal of the radio wave so as to be able to detect the communication error.

7. The transmitting/receiving method according to claim 6, wherein, when the external transmitting/receiving apparatus transmits the radio wave having an error correction code, the communication error is an error count detected in error correction, the radio-type transmitting device changes intensity of receiving signal in accordance with the error count.

8. The transmitting/receiving method according to claim 5, wherein the radio wave transmitted from the radio-type transmitting device to the external transmitting/receiving apparatus is modulated in accordance with the error information and then transmitted.

9. A container comprising:
an outer container configured to contain contents which vary in quantity; and
a radio-type transmitting device attached to the outer container, and comprising:
a power supply voltage generating unit configured to receive a radio wave sent from an external transmitting/receiving apparatus and generate an internal power supply voltage;
a transmission unit configured to transmit information to the external transmitting/receiving apparatus;
a communication error detecting circuit configured to detect communication error in a received radio wave; and
a controller configured to transmit error information corresponding to the communication error detected by the communication error detecting circuit from the transmission unit to the external transmitting/receiving apparatus.

10. A transmitting/receiving system comprising:
a radio-type transmitting device; and
an external transmitting/receiving apparatus exchanging information wirelessly with the radio-type transmitting device,
the radio-type transmitting device comprising:
a power supply voltage generating unit configured to receive a radio wave sent from an external transmitting/receiving apparatus and generate an internal power supply voltage;
a transmission unit configured to transmit information to the external transmitting/receiving apparatus;
a communication error detecting circuit configured to detect communication error in a received radio wave; and
a controller configured to transmit error information corresponding to the communication error detected by the communication error detecting circuit from the transmission unit to the external transmitting/receiving apparatus.

* * * * *